United States Patent
Yoon et al.

(10) Patent No.: US 9,211,309 B2
(45) Date of Patent: Dec. 15, 2015

(54) **METHOD FOR TREATMENT OF *ESCHERICHIA COLI* TYPE K99 INFECTIONS**

(71) Applicant: iNtRON Biotechnology, Inc., Kyungki-Do (KR)

(72) Inventors: Seongjun Yoon, Seoul (KR); Sooyoun Jun, Seoul (KR); Hyoungrok Paik, Jeollanam-Do (KR); Jeesoo Son, Seoul (KR); Sanghyeon Kang, Seoul (KR)

(73) Assignee: INTRON BIOTECHNOLOGY, INC. (KR)

( * ) Notice: Subject to any disclaimer, the term of this patent is extended or adjusted under 35 U.S.C. 154(b) by 0 days.

(21) Appl. No.: 14/316,019

(22) Filed: Jun. 26, 2014

(65) Prior Publication Data

US 2015/0004141 A1 Jan. 1, 2015

(30) Foreign Application Priority Data

Jun. 27, 2013 (KR) ........................ 10-2013-0074511

(51) Int. Cl.
*C12N 7/00* (2006.01)
*A61K 35/76* (2015.01)
*A23K 1/16* (2006.01)
*A23K 1/17* (2006.01)
*A23K 1/18* (2006.01)

(52) U.S. Cl.
CPC ............... *A61K 35/76* (2013.01); *A23K 1/1643* (2013.01); *A23K 1/17* (2013.01); *A23K 1/184* (2013.01); *A23K 1/1893* (2013.01); *C12N 7/00* (2013.01)

(58) Field of Classification Search
None
See application file for complete search history.

(56) References Cited

FOREIGN PATENT DOCUMENTS

KR 101260645 B1 5/2013

*Primary Examiner* — Nicole Kinsey White
(74) *Attorney, Agent, or Firm* — Meunier Carlin & Curfman LLC

(57) ABSTRACT

The present invention relates to a composition comprising EK99P-1, a bacteriophage isolated from nature and capable of infecting *E. coli* type K99 so as to kill the same, as an active ingredient, and a method for preventing and treating *E. coli* type K99 infections using the said composition. According to the present invention, the bacteriophage EK99P-1, an active ingredient of the composition, has a killing activity against *E. coli* type K99 and has the genome represented by SEQ. ID. NO: 1.

4 Claims, 1 Drawing Sheet

METHOD FOR TREATMENT OF *ESCHERICHIA COLI* TYPE K99 INFECTIONS

BACKGROUND OF THE INVENTION

1. Field of the Invention

The present invention relates to a composition usable for preventing or treating *Escherichia coli* type K99 infections comprising a bacteriophage, isolated from nature and capable of infecting *Escherichia coli* type K99 so as to kill the same, as an active ingredient, and a method for preventing and treating *Escherichia coli* type K99 infections by using the said composition. More precisely, the present invention relates to a bacteriophage isolated from nature which is characterized by having the genome represented by SEQ. ID. NO: 1 and is capable of killing *Escherichia coli* type K99 specifically, a composition usable for preventing and treating *Escherichia coli* type K99 infections comprising the said bacteriophage as an active ingredient, and a method for preventing and treating *Escherichia coli* type K99 infections by using the said composition.

2. Description of the Related Art

*Eshcerichia coli* (*E. coli*) is largely divided into two kinds, one of them is non-pathogenic *E. coli* which is favorably and beneficially functioning to promote digestion with keeping balance normally with other enterobacteria in animal intestines and the other is pathogenic *E. coli* which has pilus that helps the adherence of the *E. coli* to intestine wall to be proliferated and produces enterotoxin causing diarrhea by irritating intestine wall.

Diarrhea caused by such pathogenic *E. coli* is common in almost every livestock farm in Korea. Diarrhea can be caused by single infection with pathogenic *E. coli*. However, when the livestock is mixed-infected with bovine rotavirus, coronavirus, and coccidium protozoa, etc, intestinal mucosa is so much damaged as to cause acute diarrhea and to make the symptoms worse.

Diarrhea caused by *E. coli* is reported world widely, and the incidence rate differs from hygienic control level of the livestock farm. Diarrhea caused by *E. coli* is also frequently reported in Korea as well, and is known as the most representative bacterial diarrhea. The representative causative strains for diarrhea caused by *E. coli* are F4 (K88), F5 (K99), F6 (987P), and F41. Even though they are different kinds of causative organisms, they are alike to cause diarrhea in almost every kinds of livestock. *E. coli* type K99 is known as the enterotoxigenic *E. coli* (ETEC) causing diarrhea in piglings or calves. The clustering of ETEC in the small intestine of the animals is regulated by the direct adhesion of bacteria to the intestinal epithelial cells. The clustering of ETEC intervenes peristalsis, mucus secretion and movement of villi in a host to cause diarrhea.

Damage by *E. coli* type K99 infections in livestock industry is huge. Therefore, it is urgent request to develop a method for the prevention and effective treatment of the infections. A variety of anti-bacterial agents have been used to prevent or treat *E. coli* type K99 infections. However, it is also urgent request to develop an alternative of the conventional anti-bacterial agents, considering the increase of antibiotic resistant bacteria.

The utilization of bacteriophage is now highly drawing our attention as an effective way of treating bacterial disease. In particular, our interests in bacteriophage grow with the preference of nature-friendly method. Bacteriophage is an extremely small microorganism infecting bacteria, which is generally called phage in short. Bacteriophage is proliferating in the inside of bacteria cells after infection. Upon completion of the proliferation, offspring bacteriophages are coming out of the host cells with destroying the host bacteria. The infection of bacteriophage in bacteria is very unique and specific, so only specific bacteria can be infected with a specific bacteriophage. That is, there is a limitation in bacteria that can be infected with bacteriophage. Thus, bacteriophage can only kill specific target bacteria without affecting any other bacteria.

Bacteriophage was first found in 1915 when English bacteriologist Twort was studying on the phenomenon that micrococcus colony was being melted clearly by some reasons. And also, French bacteriologist d'Herelle noticed that *Shigella disentriae* was melted by something in filtrate of dysentery patient's feces and afterwards he separated bacteriophage independently by the following study and named it bacteriophage which meant 'eating bacteria'. Since then, bacteriophages corresponding to different pathogenic bacteria including *Shigella, Salmonella* and *Vibrio cholorae* have been continuously reported.

Owing to its capability of killing bacteria, bacteriophage has been in the center of our interest to fight with bacterial infection and studies followed thereon. However, since Flemming found out penicillin, antibiotics have been supplied and the study on bacteriophage has been limited in some east European countries and old Soviet Union. It was not until 2000 that the conventional antibiotics demonstrated their problems in use because of increasing antibiotic-resistant bacteria. So, once again, bacteriophage draws out attention as an alternative anti-bacterial agent that can take the place of the conventional antibiotics.

According to the recent tightening of regulation regarding the use of anti-bacterial agents by the government, interest in bacteriophage increases.

The present inventors have tried to develop a composition usable for preventing or treating *E. coli* type K99 infections by using a bacteriophage isolated from nature and capable of killing *E. coli* type K99 selectively and tried further to establish a method to prevent or treat *E. coli* type K99 infections by using the said composition. As a result, the present inventors succeeded in isolation of a proper bacteriophage from nature and obtainment of a sequence of the genome distinguishing the bacteriophage from others, leading to the completion of the present invention by confirming that the composition developed by the inventors could be effectively used for the prevention and treatment of *E. coli* type K99 infections.

SUMMARY OF THE INVENTION

It is an object of the present invention to provide a novel bacteriophage capable of killing *E. coli* type K99 selectively.

It is another object of the present invention to provide a composition usable for the prevention of *E. coli* type K99 infections comprising the said bacteriophage as an active ingredient which is capable of killing *E. coli* type K99 selectively by infecting *E. coli* type K99 and to provide a method for the prevention of *E. coli* type K99 infections using the same.

It is also an object of the present invention to provide a composition usable for the treatment of *E. coli* type K99 infections comprising the said bacteriophage as an active ingredient which is capable of killing *E. coli* type K99 selectively by infecting *E. coli* type K99 and to provide a method for the treatment of *E. coli* type K99 infections using the same.

It is further an object of the present invention to provide a disinfectant for the prevention and treatment of *E. coli* type K99 infections using the said composition.

It is also an object of the present invention to provide a water additive for the prevention and treatment of *E. coli* type K99 infections using the said composition.

It is also an object of the present invention to provide a feed additive for the prevention and treatment of *E. coli* type K99 infections using the said composition.

To achieve the above objects, the present invention provides a composition comprising a bacteriophage as an active ingredient which is capable of destroying *E. coli* type K99 by infecting *E. coli* type K99, and a method for preventing and treating *E. coli* type K99 infections by using the said composition.

The present invention also provides a disinfectant, a water additive, and a feed additive that can be used for the prevention or treatment of *E. coli* type K99 infections.

Advantageous Effect

As explained hereinbefore, the composition of the present invention and the method for preventing and treating *E. coli* type K99 infections using the same have an advantage of high specificity against *E. coli* type K99, compared with other conventional chemical compositions and methods using thereof. That is, this composition does not have any effect on other useful resident flora and can be used only for the purpose of preventing and treating *E. coli* type K99 infections. Thus, side effects are hardly accompanied. In general, when other chemicals such as the conventional antibiotics are used, general resident bacteria are also targeted and destroyed, resulting in the decrease of immunity in animals and bringing other side effects. In the meantime, the present invention provides an advantage of nature-friendly effect by using the composition containing natural bacteriophage as an active ingredient.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
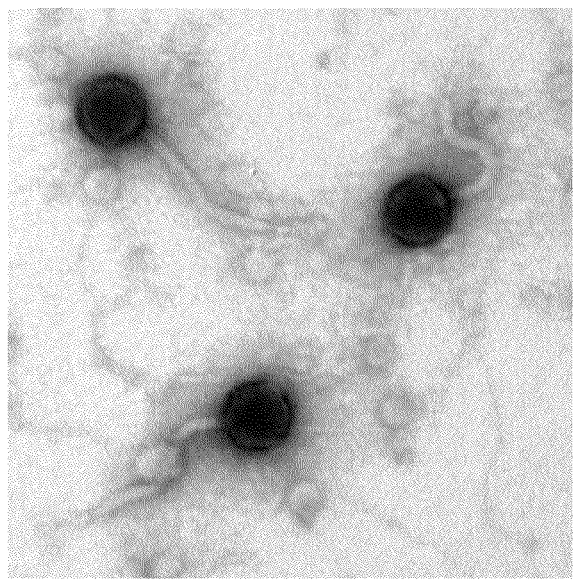
FIG. 1 is an electron micrograph showing the bacteriophage EK99P-1.

Hereinafter, the present invention is described in detail.

The present invention provides a composition comprising the bacteriophage isolated from nature and characterized by having the ability to infect *E. coli* type K99 so as to kill the same, and a method for preventing and treating *E. coli* type K99 infections using the said composition.

The bacteriophage used as the active ingredient in the composition of the present invention is the bacteriophage EK99P-1 having DNA represented by SEQ. ID. NO: 1 as its genome. The bacteriophage EK99P-1 was isolated by the present inventors and deposited at Korean Collection for Type Cultures, Korea Research Institute of Bioscience and Biotechnology, 111 Gwahangno, Yuseong-gu, Daejeon 305-806, Republic of Korea on Nov. 15, 2011 (Accession No: KCTC 12075BP).

The present invention also provides a disinfectant, a water additive, and a feed additive that can be used for the prevention or treatment of *E. coli* type K99 infections.

The bacteriophage EK99P-1 included in the composition of the present invention is capable of killing *E. coli* type K99 efficiently, suggesting that the bacteriophage is effective in preventing or treating diarrhea caused by *E. coli* type K99. Therefore, the composition of the present invention is useful for the prevention and treatment of diarrhea caused by *E. coli* type K99.

The term "treat" or "treatment" in this description indicates (i) to suppress diarrhea caused by *E. coli* type K99; and (ii) to relieve diarrhea caused by *E. coli* type K99.

In this invention, the term "isolation" or "isolated" indicates the separation of bacteriophage from nature by using diverse experimental techniques and the process confirming the characteristics of the bacteriophage that can distinguish the bacteriophage itself from others. This term further includes the course of proliferating the bacteriophage by using biotechnology in order to make it a useful form.

The bacteriophage of the present invention includes the bacteriophage EK99P-1 and its variants as well. In this invention, "variants" indicate those bacteriophages which have minor variation(s) in the genomic sequence and polypeptides encoded thereby while retaining the same general genotypic and phenotypic characteristics as the bacteriophage EK99P-1. Variants of bacteriophage EK99P-1 encompass polymorphic variants. Bacteriophage EK99P-1 variants capable of performing the same or equivalent biological functions as bacteriophage EK99P-1 are particularly preferred.

The composition of the present invention can include pharmaceutically acceptable carriers such as lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The composition of the present invention can additionally include lubricants, wetting agents, sweetening agents, flavors, emulsifiers, suspensions and preservatives.

The composition of the present invention contains the bacteriophage EK99P-1 or the variants thereof as an active ingredient. At this time, the bacteriophage EK99P-1 or the variants thereof are included at the concentration of $1 \times 10^1$ pfu/ml~$1 \times 10^3$ pfu/ml or $1 \times 10^1$ pfu/g~$1 \times 10^{30}$ pfu/g, and more preferably at the concentration of $1 \times 10$ pfu/ml~$1 \times 10^{15}$ pfu/ml or $1 \times 10^4$ pfu/g~$1 \times 10^{15}$ pfu/g.

The composition of the present invention can be formulated by the method that can be performed by those in the art by using a pharmaceutically acceptable carrier and/or excipient in the form of unit dose or in multi-dose containers. The formulation can be in the form solution, suspension, or emulsion in oil or water-soluble medium, extract, powder, granule, tablet or capsule. At this time, a dispersing agent or a stabilizer can be additionally included.

The composition of the present invention can be produced in the form of a disinfectant, a water additive, and a feed additive, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Isolation of Bacteriophage that can Destroy E. coli Type K99

A bacteriophage capable of killing *E. coli* type K99 was isolated from nature or from animal samples. *E. coli* used for the isolation was *E. coli* type K99, which was isolated previously by the present inventors and then identified as *E. coli* type K99 by the inventors.

Collected samples were loaded in TSB (Tryptic Soy Broth) medium (casein digest, 17 g/L; soybean digest, 3 g/L; dextrose, 2.5 g/L; NaCl, 5 g/L; dipotassium phosphate, 2.5 g/L) inoculated with *E. coli* type K99 (1/1000), followed by shaking culture for 3-4 hours at 37° C. Upon completion of the culture, centrifugation was performed at 3,000 rpm for 20 minutes and the supernatant was recovered. *E. coli* type K99 was inoculated in the recovered supernatant (1/1000), followed by shaking culture for 3-4 hours at 37° C. This procedure was repeated 5 times in total in order to increase bacteriophage titer if bacteriophage was included in the sample. After repeating the process 5 times, the culture solution proceeded to centrifugation at 8,000 rpm for 20 minutes. Then, the supernatant was filtered using 0.45 µm filter. The obtained filtrate was investigated by using general spot assay to see whether bacteriophage that could kill *E. coli* type K99 was included.

Spot assay was performed as follows. *E. coli* type K99 was inoculated in TSB medium (1/1000), followed by shaking culture at 37° C. overnight. Then, 3 ml of the obtained *E. coli* type K99 culture solution ($OD_{600}$: 2.0) was spread on TSA (Tryptic Soy Agar) plate medium (casein digest, 15 g/L; soybean digest, 5 g/L; NaCl, 5 g/L; agar, 15 g/L). The plate medium stayed on clean bench for about 30 minutes to let the spread solution is dried. After crying, 10 µl of the prepared filtrate was loaded on the plate medium whereon *E. coli* type K99 was spread, which was dried as it was for 30 minutes. After drying, the plate medium was standing-cultured at 37° C. for a day. It was then investigated whether the clear zone was formed on the spot where the filtrate was loaded. If the clear zone was formed thereon, it suggested that the bacteriophage that could kill *E. coli* type K99 was included therein. According to this procedure, the filtrate containing the bacteriophage that could destroy *E. coli* type K99 could be obtained.

Pure bacteriophage was isolated from the filtrate confirmed to contain the bacteriophage capable of killing *E. coli* type K99. The isolation of pure bacteriophage was performed by plaque assay. More precisely, one of plagues formed from plaque assay was recovered by using a sterilized tip, which was then added to *E. coli* type K99 culture solution, followed by culture for 4-5 hours. Upon completion of the culture, centrifugation was performed at 8,000 rpm for 20 minutes to obtain supernatant. *E. coli* type K99 culture solution was added to the obtained supernatant at the ratio of 1:50, followed by further culture for 4~5 hours. To increase the number of bacteriophage, this procedure was repeated at least 5 times and then centrifugation was performed at 8,000 for 20 minutes to obtain supernatant. Plaque assay was performed with the supernatant. Generally, the pure bacteriophage separation cannot be accomplished simply by performing the above procedure once. Thus, the previous steps were repeated again using one of plaques formed from plaque assay. After repeating the procedure at least 5 times, the solution comprising pure bacteriophage was obtained. The repetition of this pure bacteriophage separation processes was not finished until the sizes and shapes of plaques were all similar. The pure bacteriophage separation was confirmed at last by the observation under electron microscope. If pure bacteriophage was not confirmed, the above processes were repeated again. Observation under electron microscope was performed by the conventional method, which was as follows: copper grid was soaked in solution containing pure bacteriophage, followed by negative staining with 2% uranyl acetate and drying thereof; and morphology was observed by taking pictures with transmission electron microscope.

The solution containing pure bacteriophage was purified as follows. *E. coli* type K99 culture solution was added to the pure bacteriophage solution at the ratio of 1:50, followed by culture for 4~5 hours. Upon completion of the culture, centrifugation was performed at 8,000 rpm for 20 minutes to obtain supernatant. To obtain enough amount of bacteriophage, the said process was repeated 5 times in total. The final supernatant was filtered with 0.45 µm filter, followed by precipitation by using polyethylene glycol (PEG). Particularly, PEG and NaCl were added to 100 ml of the filtrate (10% PEG 8000/0.5 N NaCl), which stood at room temperature for 2~3 hours. Then, centrifugation was performed at 8,000 rpm for 30 minutes to obtain bacteriophage precipitate. The obtained bacteriophage precipitate was suspended in 5 ml of buffer (10 mM Tris-HCl, 10 mM $MgSO_4$, 0.1% Gelatin, pH 8.0). This solution was called bacteriophage suspension or bacteriophage solution.

At last, purified pure bacteriophage was obtained and this bacteriophage was named bacteriophage EK99P-1, which was then deposited at Korean Collection for Type Cultures, Korea Research Institute of Bioscience and Biotechnology on Nov. 15, 2011 (Accession. No: KCTC 12075BP). The electron micrograph of bacteriophage EK99P-1 is presented in FIG. 1.

Example 2

Preparation and Sequencing of Bacteriophage EK99P-1 Genome

Bacteriophage EK99P-1 genome was prepared as follows using the bacteriophage suspension obtained in Example 1. To eliminate *E. coli* type K99 DNA and RNA which might be included in the suspension, DNase I and RNase A were added to 10 ml of the bacteriophage suspension (200 U each), which stood at 37° C. for 30 minutes. 30 minutes later, to inactivate DNase I and RNase A activity, 500 µl of 0.5 M ethylenediaminetetraacetic acid (EDTA) was added, which stood for 10 minutes. The solution stood at 65° C. for another 10 minutes, then 100 µl of proteinase K (20 mg/ml) was added, followed by reaction at 37° C. for 20 minutes to break the outer wall of the bacteriophage. Then, 500 µl of 10% sodium dodecyl sulfate (SDS) solution was added thereto, followed by incubation at 65° C. for one hour. One hour later, 10 ml of the mixed solution comprising phenol:chloroform:isoamylalcohol at the ratio of 25:24:1 was added thereto and the solution was well mixed. Centrifugation was performed at 13,000 rpm for 15 minutes to separate layers, among which the upper most layer was obtained. Isopropyl alcohol was added to the obtained layer at the volume ratio of 1.5, followed by centrifugation at 13,000 rpm for 10 minutes to precipitate genome. The precipitate was recovered, to which 70% ethanol was added, followed by centrifugation at 13,000 rpm for 10 minutes. The washed precipitate was collected, and vacuum-dried, which was then dissolved in 100 µl of water. Genome of the bacteriophage EK99P-1 was obtained by repeating the above processes.

The genomic sequence of the bacteriophage EK99P-1 was analyzed with the obtained genome at National Instrumentation Center for Environmental Management, Seoul National University, by using shotgun library construction. Particularly, the bacteriophage genome was cut by random shearing technique using Hydro-shear to obtain DNA fragments (1~6 kbp), which proceeded to end-repairing. The repaired DNA proceeded to electrophoresis on agarose gel. Then, gDNA fragments (inserts) in 3~5 kbp were obtained. The obtained DNA fragments of the bacteriophage were inserted in pEZSeq-kan vector by using T4 ligase (ligation) to establish library. The recombinant vector introduced with the DNA fragment of the bacteriophage was inserted, in DH10B', a kind of E. coli, via transfection using electric-shock. The transformant inserted with the plasmid was cultured, from which the plasmid containing the gene fragment was extracted by using plasmid purification kit (iNtRON Biotechnology). The size of the DNA fragment included in the plasmid was confirmed by electrophoresis and the final effective clones were selected. The plasmid of the selected clone was recovered, followed by gene sequencing. Contig map was made using the obtained gene sequences by the conventional method. The total gene sequence in 44,332 bp was analyzed by using primer walking. The confirmed genomic sequence of the bacteriophage EK99P-1 was presented by SEQ. ID. NO: 1.

Based on the genomic sequence of the bacteriophage EK99P-1, similarity to those sequences of the conventional bacteriophages was investigated by using BLAST (http://www.ncbi.nlm.nih.gov/BLAST/). As a result, the genomic sequence of the bacteriophage EK99P-1 demonstrated high similarity to those of Enterobacteria bacteriophage JL1 (GenBank Accession No. JX865427.2) and Sodalis bacteriophage SO-1 (GenBank Accession No. GQ502199.1) (92%), and Enterobacteria bacteriophage HK578 (GenBank Accession No. JQ086375.1) and Enterobacteria bacteriophage SSL-2009a (GenBank Accession No. FJ750948.1) (85% and 79%; respectively) with a little but clear difference.

Therefore, it can be concluded that the bacteriophage EK99P-1 is a novel bacteriophage which is completely different from any of the conventional bacteriophages.

Example 3

Killing Activity of Bacteriophage EK99P-1 to E. coli Type K99

Figure 2:
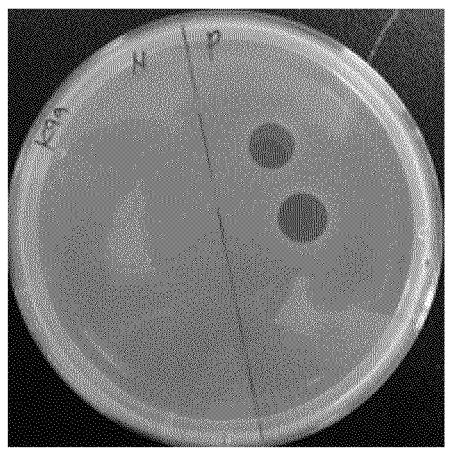
FIG. 2 is a diagram illustrating the killing activity of the bacteriophage EK99P-1 against *E. coli* type K99.

Killing activity of the isolated bacteriophage EK99P-1 to E. coli type K99 was investigated. For the investigation, clear zone formation was first observed by spot analysis by the same manner as described in Example 1. 10 strains of E. coli type K99 were used in this investigation. They were isolated and identified by the present inventors as E. coli type K99 earlier. The bacteriophage EK99P-1 was confirmed to have the ability to kill all the E. coli type K99 used in this experiment. The result of this investigation is presented in FIG. 2. In addition, killing activity of the bacteriophage EK99P-1 to Bordetella bronchiseptica, Enterococcus faecalis, Enterococcus faecium, Streptococcus mitis, Streptococcus uberis, and Pseudomonas aeruginosa was further investigated. As a result, it was confirmed that the bacteriophage EK99P-1 did not have killing activity against those bacteria.

From the above results, it was confirmed that the bacteriophage EK99P-1 can be used as an active Ingredient of the composition formulated for the purpose of the prevention and treatment of E. coli type K99 infections.

Example 4

Application Example of Bacteriophage EK99P-1 for Preventing E. coli Type K99 Infection 100 µl the bacteriophage EK99P-1 solution ($1 \times 10^9$ pfu/ml) was loaded to a tube containing 9 ml of TSB medium. Another tube containing 9 ml of TSB medium alone was also prepared. The E. coli type K99 culture solution was added to each tube ($OD_{600}$: 0.5), After E. coli type K99 was added to those tubes, they were all transferred to 37° C. incubator, followed by shaking culture, during which the growth of E. coli type K99 was observed. As shown in Table 1, the growth of E. coli type K99 was suppressed in the tube treated with the bacteriophage EK99P-1 solution. In the meantime, the growth of E. coli type K99 was not inhibited in the bacteriophage free tube.

TABLE 1

| Suppression of E. coli type K99 growth | | | |
|---|---|---|---|
| | $OD_{600}$ | | |
| | Culture 0 min. | Culture 15 min. | Culture 60 min. |
| Without bacteriophage solution | 0.5 | 0.8 | 1.7 |
| With bacteriophage solution | 0.5 | 0.2 | 0.1 |

The above results indicate that the bacteriophage EK99P-1 of the present invention not only suppresses the growth of E. coli type K99 but also even destroys them, so that it can be used as an active ingredient for the composition formulated for the purpose of the prevention of E. coli type K99 infections.

Example 5

Treatment Example of E. coli Type K99 Infectious Disease Using Bacteriophage EK99P-1

Treating effect of the bacteriophage EK99P-1 was investigated in pigs infected with E. coli type K99. Particularly, two pig groups were arranged and each group had 4 weaning pigs at 25 days of age. The test animals were raised separately in laboratory animal facilities (1.1 m×1.0 m), during which experiment was performed for 14 days. Environment was controlled in the thermal insulation facility. Temperature and humidity were regularly controlled and the floor of the pig room was cleaned every day. On the $7^{th}$ day from the experiment started, all the pigs were orally administered with E. coli type K99 solution. The E. coli type K99 solution for oral administration was prepared as follows: E. coli type K99 was cultured in TSB medium at 37° C. for 18 hours; The cells were recovered; and the recovered cells were diluted in saline (pH 7.2) at the concentration of $10^{10}$ CFU/ml. A day after the administration of E. coli type K99, the pigs were orally administration with the bacteriophage EK99P-1 (10 PFU) (bacteriophage solution treated group), twice a day, by the same method as used for the oral administration of E. coli type K99 solution. The control group pigs were not treated with the bacteriophage EK99P-1 (bacteriophage-non-treated group). Feeds and drinking water were equally given to both the control and the experimental groups. All the test animals had been observed every day since they were administered with *E. coli* type K99 to see if they had diarrhea or not. The condition of diarrhea was examined by using diarrhea index. Diarrhea index was made by Fecal Consistency (FC) score (normal: 0, loose feces: 1, moderate diarrhea: 2, and explosive diarrhea: 3). The results are shown in Table 2.

TABLE 2

Diarrhea index

| | Days after *E. coli* type K99 administration | | | | | | |
|---|---|---|---|---|---|---|---|
| | 0 | 1 | 2 | 3 | 4 | 5 | 6 |
| Control group (bacteriophage solution non-treated) | 1.0 | 1.5 | 1.5 | 1.25 | 1.0 | 1.0 | 0.75 |
| Experimental group (bacteriophage solution treated) | 0.5 | 0.5 | 0.25 | 0.25 | 0 | 0 | 0 |

The above results indicate that the bacteriophage EK99P-1 of the present invention is very effective in treating infectious disease caused by *E. coli* type K99.

Example 6

Preparation of Feed Additive and Feed

Feed additive containing bacteriophage EK99P-1 at the concentration of $1 \times 10^9$ pfu/g was prepared with bacteriophage EK99P-1 solution. The preparation method was as follows. Maltodextrin was added to the bacteriophage solution. Trehalose was added to the solution at the concentration of 5% by the total volume, followed by freeze-drying. The dried feed additive was pulverized to fine powder. For the drying process, either reduced pressure drying, drying at elevated temperature, or drying at room temperature could be used. For the control experiment, bacteriophage free feed additive was also prepared by using buffer (10 mM Tris-HCl, 10 mM MgSO4, 0.1% Gelatin, pH 8.0) alone which was the same buffer as the one that was used for the preparation of bacteriophage solution, instead of bacteriophage solution.

The above two feed additives were mixed with feed for hog respectively at the weight ratio of 1:1,000.

Example 7

Preparation of Water Additive and Disinfectant

A water additive and a disinfectant were prepared by the same method because both were formulated in the same form and have only difference in their use. The water additive (or disinfectant) containing bacteriophage EK99P-1 at the concentration of $1 \times 10^9$ pfu/ml was prepared. The preparation method of water additive (or disinfectant) was as follows. Bacteriophage EK99P-1 was added to the buffer which was generally used for the preparation of bacteriophage solution at the concentration of $1 \times 10^9$ pfu/ml and then well mixed. For the control, the buffer itself was used as the bacteriophage free water additive (or disinfectant).

The prepared two different water additives (or disinfectants) were diluted with water at the ratio of 1:1,000, resulting in the final water additive or disinfectant.

Example 8

Investigation of Feeding Efficacy in Pig Farming

Improvement of feeding efficacy in pig farming was investigated by using the feeds, water, and disinfectants prepared in Examples 6 & 7. In particular, this investigation was performed by observing death rate. 30 piglets were divided into three groups (10 piglets/group) (group A: supplied with the feeds; group B: supplied with the water; group C: treated with the disinfectants). The investigation was performed for 4 weeks. Each group was divided into two subgroups of 5 piglets. Those subgroups were either treated with bacteriophage EK99P-1 (subgroup ①) or not treated with bacteriophage EK99P-1 (subgroup ②). The test piglets were 20 days old. Each group piglets were raised in an isolated cage separated from each other at regular intervals. Each subgroup was sorted and marked as shown in Table 3.

TABLE 3

Subgroup sorting and marking in feeding efficacy test on pig farming

| | Subgroup sorting and marking | |
|---|---|---|
| | Bacteriophage EK99P-1+ | Bacteriophage EK99P-1− |
| Feed | A-① | A-② |
| Water | B-① | B-② |
| Disinfectant | C-① | C-② |

The piglets were supplied with the feeds prepared in Example 6 and the water prepared in Example 7 according to the conventional method as shown in Table 3. Disinfection was performed with the conventional disinfectant and the disinfectant of the present invention by taking turns, three times a week. The day when the disinfectant of the present invention was sprayed on, the conventional disinfectant was not used. The results are shown in Table 4.

TABLE 4

| Group | Death rate (%) |
|---|---|
| A-① | 0 |
| A-② | 40 |
| B-① | 0 |
| B-② | 40 |
| C-① | 0 |
| C-② | 40 |

From the above results, it was confirmed that the feeds, water and disinfectants prepared according to the present invention could help to reduce death rate in pig farming. Therefore, it was concluded that the composition of the present invention was effective in the improvement of feeding efficacy in pig farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating *E. coli* type K99 infections in a subject animal, comprising administering to the subject a composition comprising the bacteriophage EK99P-1, harboring the genome represented by SEQ ID NO: 1, or variants thereof.

2. The method of claim 1, wherein the composition is administered to the subject animal in the form of a feed additive, a water additive, or a disinfectant.

3. The method of claim 1, wherein the bacteriophage EK99P-1 corresponds to Accession No. KCTC 12075BP.

4. The method of claim 3, wherein the composition is administered to the subject animal in the form of a feed additive, a water additive, or a disinfectant.

* * * * *

SEQUENCE LISTING

<160> NUMBER OF SEQ ID NOS: 1

<210> SEQ ID NO 1
<211> LENGTH: 44332
<212> TYPE: DNA
<213> ORGANISM: Bacteriophage EK99P-1

<400> SEQUENCE: 1

```
tataatccca cttagatggc agggccgtct cctatgttgc cgatggtcgg cgcatatgca      60
caaaagggct tatatcatgg cagaaattaa agttaaaggc cgtcgagcta aactggacgg     120
acgagtagca gttaccccgc gccgtaaacc aggcgagcaa accgagcata ccaatctcgg     180
acctgaaatc gagtacggaa agcgccgtaa aggcggcaaa tgtggacgcc ctactgacta     240
ccgatccgtt tactgcgacc agcttcgccg ctattttgcc gacgccgacg cctggcaggt     300
caactactcc gataaaggcg ctgcgcaagt aatccccgc aacaaatgc caaccttcgg      360 cagatttgcc gcggaaatag gtgtgggcgt tgcctgcctg taccgctggg cgcgcgcaca     420
tgaggagttc gccgaggcta tggcggacgc tatggaattg cagaaaactt tcctgatgga     480
agctggcggt gtgactatcg cggcaggctt cgcgaccttc ctgctcaaag ccaaccacgg     540
cgtacgcgac gatatcccac tggatgacga cgaagatgat aacggcgacg tcgttgtcga     600
acctaccggc aaaggccagg gcgaataatg cgtaactatg ctgcagaaca ccgcgcactg     660
gaacgcgcga tcgcgaagcg caaccgacca ccgcgcccga cacgcgttgc gcaggcggtg     720
cggctttacc agcctgattg cctaccgcac caggtcgaac tactgcggga cacgaagact     780
aaaatcctcg gcctgtgttc cggcttcggc ggcggcaagt catgggtcgc agcccgtaag     840
gtaatccagc ttttaaccct gaacccgggt catgatggca tcgttacaga accgactatt     900
cccctcctgg ttaaaatcat gtatccagaa ttggagaagg ctttcgacga ggctggcttc     960
cggtggaagt tcaacaagca ggacaagatc tatagcgttc tggtgaaagg caatggacc    1020 cgcgtgatct gtgaatcaat ggagaactat acccgtctga tcgggtcaa cgccgcgtgg    1080 attgttgccg acgagttcga caccacgaag caagacgtcg caatggcggc ttatcacaaa    1140
ttgctcggtc gtctgcgtgc gggcgtggtc cgtcagtttg tcatcgtatc cacgccggaa    1200
ggcttccggg caatgtatca aattttcgag gtggagaagg atagccagaa acgtttgatc    1260
cgggcgaaga ccaccgacaa ccaccattta ccggcagact ttatcgacac gctgcgcagt    1320
cagtacccgg cgaaccttat tgacgcgtac ctgaacggcc tgtttgttaa ccttacgtcg    1380
ggcgcggtgt acaagatgtt taatcgcgag gagaacgcca gcaccgaaga agtacaaccg    1440
gaagacacgc tgattatcgg tatgactttt aacgtcacga aaatggcggc ggtcgtgtat    1500
gtaagacggc agcgtaccac cgagaacaag gagttccgcg acgagattca cgccgtggat    1560
gaattcgtgg acctgtttga taccccggct atgattgaag cgatcgagga gcgctacccc    1620
gatcattgcg ctgccggtaa ggtcgtcgtg tacccggata gcagtggcaa gtcgcgtaag    1680
acggtcaacg cgtcgtcgtc cgatatagcg caactggaag acgcaggctt cgaggtggaa    1740
tacgacagcg ttaacccacc ggtgaaagac cgattgatcg cgatgaatac gatgatgtgc    1800
aactcgaagg gcgtgcgcca gtattttgtc aacctggata atgccctac actagcgaaa     1860 tgtctggaac agcaggttta cgacctgaag aaaggcgagc cggataaaac cgccggtgtg    1920
gaccacatga acgatgccgc gggttatcca attgcgcacc tgttcccagt gattcgccca    1980
atcgccgttg ttccaactgt agacttctac taaggaaacg accatgaccg ttaacgttga    2040
caaccagcac ccgctctatg cgcgcatcgc gccagagtgg aaaatgatcc gtgattgtgt    2100
```

```
ggcagggag  cgcgccgtga  aggcgtgcgg  cccttgtac  ctgcctcatc  ccgccagtgg   2160
cgacaacact  gacccgaaag  cacgggcgag  atataaggcg  tataagcaac  gcgctgtatt   2220
cctgaacgcc  accgcccgca  cacttaacgc  actgttaggc  gttgccttcg  ctaaaccggt   2280
aagtctggac  ctttccgggg  cgattgcgga  ccttattgac  gacgtagacg  gcagtggtat   2340
gccgctgccg  caactcctgc  gcggtgctat  gtcggaagtg  ctgcaatcag  gccgtgcggg   2400
ctttatggtg  gactacgatc  gccaggcgca  ttttgatgag  ctgggtaacg  tagtgccgca   2460
gacagccgct  gagatggcgt  cacaccgccc  acttatccgc  ctgtacacgg  cagaacagat   2520
catcaactgg  cggcagaccc  acggcgtaga  tacgctaatt  gtgctaaagg  aaacggacga   2580
aatcagcacc  gaagacccgg  acgacttcgc  aaaccacgaa  gtaacaatat  ggaccgagct   2640
tcgcatgatt  aacggtgcgg  cacacgcccg  ccgctggttt  tataacgcgg  acacgtccga   2700
ggtgcaaatg  gacttgccgc  gtggattcac  ccgcaccgac  ctggtgccgc  tggtggatgc   2760
ctccggtaag  gcactgactc  aacttccgtt  ttgctggtgt  ggcgcggtgg  acaacaacgc   2820
gacgccagac  gccgctccgc  tggcagatat  cgcatccatc  aacattaagc  actacaacgc   2880
cgaagcggac  gtcgccgaga  tcgcgcacat  cgtgggccaa  cctaccctgg  ttgcgacggg   2940
cttgactcaa  tcatgggcgg  acaaaaacct  gaaaggcggc  atcgcgctcg  gagcgactaa   3000
gggcgttatt  ctcggtcaga  acatggatgc  taaactgatc  caggcgagg  agcgcaactt   3060
gtctgttgca  ctgtgtgagc  gacgcgaatt  gcaaatggct  aaactgggcg  cggccctggt   3120
tgagaagggg  actgcaccta  agacggcaac  cgaggcggcc  tacgatgcgc  agactgataa   3180
cagtatcctg  tcgcttattg  ccagtaacgt  tgagaaggct  ttcaaccgtg  cgctgcaaat   3240
cgtgcagcta  ttcacggggg  acaccgcaga  tcaacgtgta  acgctgaata  agttctacac   3300
cgagatcacg  gttgatgcac  agcttatgac  cgcgatgatg  gcgggtgtgc  agacgggtac   3360
ggtccgcctg  gcggacttca  tcaagtggat  gatggcgcag  ggcgtcatcg  acgactcgca   3420
aaccgtcgag  caggttgaag  acgaattgcg  aaatcagaat  ccattgcctc  aaatgtcccc   3480
ggatgcggta  gaatctaccg  aagaagaccc  ggacaaggta  gcggacaatg  gcgaagacaa   3540
ttaatcaata  tatggcggat  cgaatgattc  gccgacacat  cttcacccag  cgcctgagta   3600
atgaccaggc  gcggcgggtg  ctggctatgt  gggagaagtt  ccggcccacg  ttactgggta   3660
agctgaccga  gttacttgat  ggcaaaaagt  ccatgaacaa  caaggcactt  accactctgt   3720
taacgcaact  cgacaagacc  gtcaaaacgg  aactgcgcac  cgagtttaag  gcgttggctg   3780
aaaagccttca  ggagttcgcc  gacaccgagg  ccgattatct  cgccgacaca  ttaacggcag   3840
cgatccagcc  ggtggtcgcc  gtacctgcgg  tcgaggtggt  tggcgtagtg  accggtgctc   3900
agatcgcagc  tactgcaatg  aaaaacccgt  tccaggtaa  caccatgatg  cagtggcccg   3960
attcactttc  cgagtggacc  aggacgcaga  tcggcaatca  ggtgcgcgcc  ggattcatcc   4020
agggcaagcc  gacgatggaa  attatcgcgg  atgtgaggcg  cacgctaggc  ggtcgtagtg   4080
cgcaagcaat  ctcaagcgtt  gttaagtccg  cggtcaacca  ctatgcggcg  accgcccgcg   4140
aattaatggt  aaaagctaat  gacgatattc  tcgaaggtcg  ccaatggttg  gctacattgg   4200
acactcatac  ttccccaatg  tgccagctac  gcgatcgcct  gttttatcct  gttgacgtca   4260
ctcccgacac  caaaggcaag  cgcggcggga  aagtggtggc  gggatcacaa  tatggcgctg   4320
gaccgggcaa  gctgcattat  tgctgccgtt  cgacggagac  gtggaaagtt  aagggcatgg   4380
aagattggcc  cagtggtaag  cgtccggcac  tgaagcctga  cgcgggccga  ttgctgagtg   4440
```

-continued

```
agcaggtcga cgcgcggact gatttcttct catgggtgca gcgccagccg cgccatatcc    4500
tggaggaatt atatggagtg caacgcgccg accagattat gcgcggcgtg aaagtgccga    4560
agatgtttac cgattctggc gaactgatga ctattgcaca gcttaaaaac cggggggctat    4620 ggcgtgatta agtatgcagc tattggactg gttataggtc tggcggtagg attctggcta    4680
ggtgactcct atcgcgctgg cgtagtggcg gaggcggcgc aagaagcgca agccaaagcc    4740
caacggcagc aaactaaagt tgttgagcga tccgtgcagg ccgaacaagc ccgcgacgta    4800
gaataccgga ctatcacgaa agaggttgtg aaatatgtta cgcgtcctaa ccgtcctgat    4860
tgcagttttg atgctgagcg cgtgcggatc aagcagcgtg ccgttgatgc cgctaacgga    4920
gtcggcactg cgaccgccgt gcaagttcga taacccgtcc gcggaccccg acgaagattt    4980
gatgattgac gtgaaaaata tggaatgcgg ggcgaagctg agggcgcagg tcctggagtt    5040
gcagcagata attcgggggc cgtaatggcc ccctttttatt agcgcggaat accgcagatt    5100
tcgtttaacg tcttcacgtc cagtgccacc gccgtggact tcggcttgtc cgggtatgga    5160
ataaactgtt ccacttcagg ccacgccttg atcagcttct tatcggtatt gtgcatatcc    5220
agcacgccgg tcacagtcag cttgaatgcg tcatacttcg cacgcaactc gcggcgggcc    5280
ttgtcgttac ggtccaggcg cttgcagaaa tcatggtccg ccgggtagtc tatacgaccg    5340
catgacttat atatcggcag cgcttttccca tcctcgtcca cttcgcacac agaagccagc    5400
attacttctt cgtaccctgg tacaatatcg ccgagatctg gagatagcgt attcatgtat    5460
ttatattccc agtatccgcg atgtactcgg tattgtcgtc cgtcaccgct caatgacagt    5520
gtgcgcacat ttccgcccgc gttgatttcg aaagtggcgt cgtaaacgct gccgatgcct    5580
tttgggcggt cagcattata tctatacgtc gccttgttgg tgtatacgct tactccgtac    5640
atctgcgacg ggtcatcgcc gattgcttta atgcgcgcga gtagctcggc gaaagtgcga    5700
atgccttccg gcatacagtc cagcgtaatg gcgtacgcca ggtcgcgcga gtccatcatg    5760
atggatttgg cttcggtcgc gatttcatgg tcgcgcagga tgttagccag aatctggttt    5820
ttaatgtctt tcgtcagtct catttgtgtg tcctctttta gtggttgtat aattcgccgc    5880
gtgcgtcggc atcttccatt tggtgtagtg cgtgtttctg gtcctggcaa ggaatccagc    5940
gttcctctaa tttatgccag aagtaaaaca ccccgttatc cagcttaatc tcggcaatac    6000
cgttattgaa agttagcatt tgttacccct catttgttgg tatgcaacca atatactgca    6060
accaatccac caatgcaagc aaattttgcg attattttta tcgctgataa tattagaagc    6120
gtgaagtcga gcgggtggcc tgctctgcca caatcccagg gggatagcat gaaacttact    6180
aaagcagaat atgacgcgtt gccggaaggt atgaaggcgc ttttttgttgc cgatggcgac    6240 gggtataaat caacgttcat gaccgcagaa gaagtacagg cggaaatcaa gggtctgaaa    6300
gacaacaacg ctaagctggt gagcgagaag aaagcagaag ctgaacgccg cgccgaagct    6360
gagcgccttg cgaaagagaa agaggaagcc gccgcgcgca aaaatggcga cctcgaagcg    6420
atcgacaagt cctggaaaga taagtttgcg aaacacgaag cagacacatc gggaaaaatc    6480
gaagcctacc gcaagcagat ccacgatcta accatcggca gcgctgccaa agacctggcg    6540
tcgaagctgt tcgtaagaa tgcgggcatc atgcaacgcc acgtaatgga ccgcctgacg    6600
ctggaagacg gcgaagacgg cagcttgaaa gtgcgagtct tgcaggatgg caaaccgtcc    6660
gcgctgacta tggaagagct ggaaaaagag ttccgtaata cgccgatttt tgcatccgtc    6720
ctggctggca cgccagccgg tggcgcgcct agcaaaccga cgcaggttgt cgaagatgtg    6780
aagtcgaaaa tcactatggg ccacagcttc ggtatcactg accttacgaa acaggcaggt    6840
```

```
gaaatcatcg ctaagatggg cgacgacgag taagcagatt gcccgcgaaa gcgggcaatt   6900
ttgcgagcgc gtaaatctaa ggtaacatta acgtcactgg gcgaatgctc acaactcaaa   6960
ggatttcgat atgtctttaa cagtgttcca gcgtaaactc gttaccgcgg ttacgcaaat   7020
gatccccgac aacctgaacg ttttcaacgc tgccgccaat ggcgctgttg ttctcggtac   7080
tggtgaagtg ctgaaggacg ttgtagaaaa aatgtccgta ggcttgatcg ccaacctcgt   7140
taccgaccgt aacgcctatg ccctgtcgg tactccggcg accgcaaaag tgctggcgcg   7200
tatgctgacc aactccgtca acctgtccgc gaaagtgggt ccggtagcaa tcactaaggc   7260
tatgatggct aaaatcgaaa ccaacgttaa cagcgttgcg gctgagattg cggcacaggc   7320
tactcaagcg attatgctgc attacctgaa ggctggcatc ggcgcaagta aagcggcgat   7380
cgaaagcaac gcagcggcaa aatacaccca accggcgcgc gttgacggcg ttggcggtcg   7440
taccttcccg accctggcag acttcccgct ggcggcttct aagttcggcg atcaggcgtc   7500
tttgattaag tcctggttta tggacggcgt tacctgggca aacttcattg cgtaccaggc   7560
actcccttcc gcggaacagg tattcgcaat tggcgatctt caggtaatgg gtgatggcct   7620
gggccgtcgt ttcattatct ccgatgccgc tgctgatgct atgggcacgg gtaacatgct   7680
aggtctggtc cctggcgcgg ttgccgttac caccaacggc ctcgatatgc tggcgcagga   7740
gaaaggcggt aacgagaaca tcgaacgctg gtggcagggc gagttcgact tcaacgtggc   7800
tgttaaaggc taccgtctga aggcgtccgc tcgtacaccg atcgaaggcg tacgctcgtt   7860
caagctgtcg gatatcacca cttccgctaa ctgggaactg gaccaggcc aggtagacaa   7920 cgcaccggca accgtgcagg acgttggcga tgttggtgat ggcgatacta aaggccgtcg   7980
taagacccag gcagcacagg cagtgccgac ccgtcacatc aaggaaaccg ctggcgtact   8040
ggttacgctg acggcgacta ccgcgtctta acgggcgcac atcccaaatg gcggggctta   8100
tgcccgcctt ttttatagga gcaaataaga tgtatggcga cccgcaaacc tttgtcgatt   8160
atgccgctgc gcgaggcgtt gaaattacgc tgggcgatgc aactcgacac cttaccgtcg   8220
ttaatgactt ccttaacggc atcaactgga tcggcgaaca agcggaccag accggaatcg   8280
acgcatggcc ccgcatcaat tacccatcgg acggtaagcc ggtgcgcgac acgctaaccg   8340
aagtcgtggc ggtagtgcct gtcgggcaaa tcgtagactt tgcatcaatc cccgttgccg   8400
ttgagcaagc tgtttaccgg ctggcgctgt ggtggcgga cgagatcgat atttctccgg   8460
tcggcgatgg taaagagact atccgcgaaa cggtcggccc gatcacgatg gaatatgacc   8520
cggcgtcgat tggtagcggg gtgtcgttcc cgtggtggga tggcttgtta ggccactggg   8580
ttgattcagg cggcaacgcc gcaggcaatt tcgacgtatt caggggtaa tatgaatcct   8640 gcattactcg cggcgataat cgccgccaac actaaacagc cgccgaaca agaaccggag   8700 ccagaacaag tacaaccggc acaggagagc gaagaagatg gcgggcttta attacgcagg   8760
attaaagcgg aaagtgaatc cgctgattaa aaaattcggc atgaccgtta cggttacgcg   8820
tccgggatcg gttgaccgtg tagacggcga cgaagtggta atcccgccaa cgtcgtttga   8880
cgtcatcggt cttcgcgagg agtacaagcc tagcgagatc gacggaacgc gtatcgttgc   8940
cggtgatgtg aagtttttat gtcgggcggt tgagcaattg cgggtgggcg accttgttaa   9000
cctgaacggc actgactacc gggtcgtcaa cccgaaccca ctgcaaccgg ctggcactac   9060
catgctgttt caactacagc taaggggcta acgtggctga agtctactca ttcgccgcca   9120
ctattgctac gtgggtggat aagacgaagg agaacaacga taaggcggtg cgggcgtacg   9180
```

```
gtatgcaaat actcggacgc cttattgaaa tctccccggt gggcgatccc cgccggtgga    9240
agattaacaa ggcttacgcg atgggcccgcc agcacgcgaa caaggtgaac gccgcacagc    9300
gccgcaagaa tggcggcaaa ctgaagcgcg ggcagaagaa gcacgccagt gtgctcatct    9360
cattcaaaac taaaaacggc aacgtcacgt tccgccagcg tggctgggcc gcgaagaatt    9420
acaccggtgg gcgcttccgg ggaaactggc aggttacgtt cgaccgcccg gctgtcggcg    9480
ctattgaccg cgtggacaag gccggaactg caacattagc cgcggggcgt gaagtgctgg    9540
cgcattacga ttccggtgaa tacgggtcga tctggtttac taacaatgtg ccgtatgcgc    9600
agcgacttga gtatgctgg agtaaacaag cgcccgcggg gattgttcgc gtcgtagcgg    9660
cagaaatcaa ttcgaaggtg aaataatgag caatactcta atccgcaagg cgcttaacag    9720
cgttgtcgaa gagctatcgg ttagcctgag cactagcgcg cgcccgataa aggttaactg    9780
ggagaacgtg agcggcgacc acgcaaacgg cagcggtgtc tacctggaac catatttgct    9840
tccggccccg acccagtttg tgggcttcca gcagaagggc cggatctatg caggcgtgta    9900
tcaggtcgcc gtggtatttc ctgcgggcac gggcacacag tacgcgagcg aactggcgga    9960
cgccatcgcg acgtctgata agtggcgggc cgtaagactt accggtgctg cgttccagct    10020
tcaggacgcg ccatacacca gttcggtgat tgaggatgtt gatcgtgccc gcatcgtggt    10080
tacagtaccc tacacctgtt gcgcctgatt tggcgcaatt ctatgcgtgc ggtatcatta    10140
atccgtatat ctaaacagga gcgtcattat gggttatcaa cttcctaacg ggtccagcgt    10200
ccagattggg tccgtactgg gtagcggcat cgctgttacg gcagctacca acgccgccgc    10260
gtctatctct gatcttacga aaggttgcgt tatcacctgc gcggcttctc atggcctgaa    10320
agtcggcgac gtggtaatgt tcactaaaac cccgtgggta cgtgcgctga accgagcgtt    10380
catcgtgggt aaagtggcta ccaacgacgt tacgctggcg cgcttcgaca cctcggacgt    10440
gaccaaatat cctactggcg cgtttggggc aggcactccg ggcgaagtgg tgaaggtgtc    10500
gagctttatc gacttcccctt tcattactaa cgttgccgta tccggtgggg atcagcagac    10560
gaccaccttc cagccgttac aggtgaacac cgcaatcagt ctgaacacca cgaaaaaccc    10620
gtttgttcag acttacacct tcacccacga cgaagaagac ccgatccgcc caatcctgga    10680
agacctggac ggcacacaga aaaccactgt gattaagttc actaacccgg cagcggcaag    10740
cggcaaaggt gagatccgta tttacccggc taaggtatct ttccagaaga ttccatcggc    10800
tgaagtaaac aacgtggaga cggtggagtc caccctcact atgcagtccg atatggttat    10860
ttaccgtaag gacctggttg aagcgctgtc gtaatttggt cgcttaaata gcgggtgtta    10920
atatggggcc agtacggccc ctttttttatt ggagaattac ataatggcta aagcaccact    10980
ctttacactt gaccctaaac cgacttttaa gctaccgatt gagatcccgc gccccggaga    11040
aaacgaacct ggcaaaatga cgtttaccgt gcgccaccgt ccgatcgacg agttttcgca    11100
gaccatgcag gatactgagc gcaagttgtc agaatatgac gacaatgacc cggacggctt    11160
taatgttatg gtcgaggcca tcatgcacgt cgcagaaggc tggaatctgc cggacgaatt    11220
taacgcggag aacgtccgcc gcttggtggt caactacccg cgcgcgttcg gcgtgttcca    11280
tacgtcgtac tatctcgaac tgatgggatt gcgtgaaaaa actaattga ggcggcgcga    11340 cgcttttatg gcccgccgcc accctccgaa gatttagccg cgagtttatg gggcgcgaca    11400
cctgaagacg tgtgtccgcc cgttgcgctg tggcccgaca acgcgaaggt agtcgcagtc    11460
ttcacagatt gctccacgca atggcgtacc ggatttggcg gggcatacgg catcgactac    11520
ggcgtactgg aatggttatt taagatgcac ggcatcgaaa acgcgcaacg tgcgtttaaa    11580
```

```
gatatcaagc taatggaacg cgttgcgctg gatgaaatgg cgcggcagaa ccccgcataa   11640
cgaagcggga caggcgggaa gtaccgtttt gtcccgcctc tgtaaaaccg catatctaat   11700
cactttcatt gcataaactc aaagcgggac aggcgggacg tcccgttttg tcacgccctg   11760
taaatgtgca tacctatgca gatttcgtgc ataaaccaaa cgggacagaa agcgggacaa   11820
acaagaggcg ggacaaagcg ggacagcacc ccgtcccagc cagtgctgcc gcggttttca   11880
gccgatcggg acagcgggac agcaccccag tctttcagac tagacggggg tcagtggccc   11940
ccctcgtctg agactgaata aggtttgttt tgaaatcgct gatacaatat ccatcggcaa   12000
ctgcataaaa aagggactg cataatggca gatcaggcag caggcatcac gctaaaggct   12060
gatgttgcac aaatcagaac ggcaaatact gtgctggact ccttcgcaca gaaatccgag   12120
aacacagaaa acaaggttaa gaattaaac gacaccctcg gcaaatccaa aaaggtgacg   12180
agtgacgccg cgggcggaat ggagaagctg gcgactgaat cgcagcgcgc cgccgatggc   12240
atgacgaaac aggagcgact tgccaacagg ttaggcatgt cgaccaaaaa cctgggcttt   12300
gcctcgcgta acgccgcatt ccagttacag gatatcgcag ttacgcttga gatggggatg   12360
cctgttcacc gcgtcatgct tcagcagtta ccgcagctaa ctggggcgtt tggcggactg   12420
ggaaacacgc tgcgttatgt cgtcggcaca ctcggcccgt tagggattgg catcgctgca   12480
ttaacggcaa cgctcggcgt aggggtggca attacgaccc cgcgagagaa ccaggtggcg   12540
gcgcttaata agacgctggc gctgtccggt aatatttcag gcctgacagc taaccagatc   12600
cttgtgctgt ccgagaacgc cgagcgcatg ggcgggtcat ttcgcaagac gcgtgacaca   12660
atccaggcgc tggcggcggc gggtgtgaaa gcggtggtg actttggcgc attggctaag   12720
gtagtgaatg actttgcgaa ggtgtccagc cagccgatcg aggatgtggt ggcggcggtg   12780
gcgaagctgt caaccgaccc ggtaggcggc ttgcgcgcac tggcggataa gtatcacgtc   12840
gtaaacgaag cgcagatcca gcaggtacag tcgctggttg atgcgggtcg tgagacagac   12900
gcagttgcgt tggctaacaa acagccgct gcgtcgttca ccagcatgac caatgagatc   12960
aaggcgaaca tgggcacgct tgagcggtct atgaacgtcg tcacatcggc agctaaatcg   13020
atgtgggacg ctatcctgga tgtgggccgc gcgcagtcct ccaatgagtc cgagatgaaa   13080
gcgcgcgaat cactacagcg catgaccacg gcatactatg ccgagatgaa agcggtaaac   13140
gctgccggtg gggtaatgac cgaagcgcag aaagcgcgta ttaacatgct ttacagcgaa   13200
ctggtcgccc aggaaaaagt agtggcgtcg ctcaccctgc gtaaccgtgc ggagcgagac   13260
aacgcccgcc ccgcggacga atcagcaaag gcgaacgagg aggccaaccg caccgctcgc   13320
gaccgcgccg cgttcgagaa ggagtacgca actaacgcga agaagcgcgc tgacgagatc   13380
gcccgcctca atttgctgaa taagcgcggc gttatcgacg agaaagagct tgctgaggcg   13440
gtgaagcagg taaacgagcg ttacaaagac cccgccccga agaaggccgc ggctgttcgc   13500
gtggatgccg gtatgaaaat gctggaagtc gcacggagcg aactggccca gcttcgagaa   13560
tccggcaagc agatcgaagc caacgcatcg acgcagaccc gaacgcaacg cgctcaagcg   13620
gccttaaaca agctgatcgc ggataatgag cagttaatcg ccgcaagcaa agaaagagcg   13680
ctaacggcag ccgaaaagca gcaattagtc gagttcgggc gcgtgaagga agtccgcgag   13740
cagatcgtcg aagaagccaa attgctggac gcgaaagaga agcaggttaa ggcgcacgcg   13800
cagatcgatg ccttcgttaa gaaccagaac gccgaactaa aagccaccgc cgcgggctat   13860 gcccttttcca ctcgcgaagc ggcaaacctg cgcgaagaat tgcagctaat cgaccgcctg   13920
```

-continued

```
aagcgtgtag gcgctaacga taccgatatc gacaaggcgg tgtctaagct gcgagaagtg   13980
caggaagcac agaccggcgc taacgcctcg ttatgggatg gattcagtcg cgggcttaag   14040
gatagcgtgg atgagatggg taacggatat acgcagatgg cgtctctcac gaaattcaca   14100
ttcagcgcta tgcaggacac gatgaacgag tttttcgaga ctggcaagct gaacgcaaag   14160
gatatggtta agtccatcct gagcgaatta atcaagctgg ctacctcgca ggcgttcaag   14220
tccatcgtta gcgctttcgg tggtgacggc ggcaaaaacg gattgttcgg cgctatcttc   14280
tctggcctta ctaagaatgc ggacggcgga gcgtacgcag gaggcaatct cgcggcctat   14340
tcggggaaag tggtaagcca gcctaccttt ttcagttatg cgtccaggc gttcgctaag    14400 ggcgctgggt tgatgggtga ggctggaccc gaggccatca tgccactgaa gcgcgggccg   14460
gacgggaaac tgggcgttgc cgcgtctggc gcaggcggtg gtatggtcgt gacgactaac   14520
gtttacacgg ggactggtaa aacgatacc agtgtcagcg ggccggaccc ccgtactgcg    14580
caagcgttcg gcaagcaaat aaccgaggcg gtgaaggccg agatcgtgaa agctacgaaa   14640
ccgggtggag tactttacaa acgatgataa aatggccccc acatccatcg tgggggatct   14700
tctatggcac aaggtacaat cacactaacg aacggaagta agaccgtcac gggcgcggga   14760
acggcgttct tgagcgaggt cgggaaggta cgcgtattcg cccgcatcga cggcaacgac   14820
tacaccggaa aaattgcggc attcaactct aacaccgtca tcactctggt ggataactgg   14880
gccggtccaa cgaaatccgg tgcggtatat gagctaatcg aagcacacga cccgcgatca   14940
aacgaatggc cctattactg gcacatgcaa ttgcaaggcg gcggagacgt gcagttggct   15000
ttccggtccg aggaattgca attcggtaac ggttacggac agaacattgc ggacggcccg   15060
aacgccgaaa cgaaacagtt ccccgtgcaa ttcataggac tgactaccga caagtggtgc   15120
aaccctaaac tggtttacaa cttccttcgc gggcacttcg taaaaccgtt catcgtcacc   15180
gcgccggatg gcgaaacagg tttattcgtg gtcgagcgct cgagcttgtc gtacactgac   15240 aacgacact acacgcaac tgtatccgcc acccttaaga ctgctattgg attcgtaaga    15300
tgaataaact ttatcgcgag gcgacgcgct ttgacccatc gggccgcgtt cgcctgattc   15360
acattgacgc gcaggacgtg gaaccaggcg acggcgcgat cggagcgggc catcactatt   15420
ttcattactg ctttattcca cacactgccg aggatattgc tgccgctggt ggtgacgagg   15480
ataagctaaa acccaaatca atcttcttcg gcgggcagga gttcgaattt tggcccttcg   15540
atctgtctgg acttaacttc tccacctcgg cggcagcaga accgcaacta acaatcgtcg   15600
atattggcgg cataataacc cggctgtcgc tgaaccacga ccagctactg ggagcgaagg   15660
ttgagatcat tgatacgttc gcgaagttcc tggacaacgg gacagatcca gacccgacgc   15720
agaaacgagt tcaggagtat tacatcgact cgcaggtcgg gcgcaatcct ggcaagcaaa   15780
tcaccttcgc actatcctcc cccgcggata tggaagggca ggtcgtcccc cgtcgccaaa   15840
tcatgaatat gtgcgaatgg gcgctcaacg ggaagtacgc cagcggggac gggtgcacct   15900
ggaaccttgc gaagcccggt atcaagtatt acgacgagcg aggtaatgaa gtcattgcga   15960
tgaatatgga ccgatgcggc ggctgttttgt ccgactgcta tcttcgtttt gggcaagggc   16020
ttgcggaccc taaagcggcg gtgttggact tcggtggttt tcctgggtcc aaattgatta   16080 agggtagcc atgttaacga aaaaggttaa aagcgatatc gccgcacacg ttgcggcgtg    16140
tctgccggaa gaagcctgcg gcctggttgt catggttggt cgtaagcaag tattcgtccc   16200
atgtctgaac gtattcgaag acccgaccgg cgtgcgctca cgcaaggacg cgtttactat   16260
tagtgatatg gcctggatgg atgccgagga tatgggcgac gtcgtgcgcg tagtccattc   16320
```

```
gcatccgggc cagcgagagc ttaccccctc actgggcgac gttaatggat gcaacggcag    16380
cggcgtagtc tggaccatca ctaacgaata tggcgacttt atcgagatcg accctgaaga    16440
cccgccgctg gtaggccgcc gatttgttct cggaattacg gattgttacg gcctcgtaat    16500
ggactggcac aaaaagcagg gagtaaacct gccagacttc cgcgtgccgt ataactggtg    16560
ggagacaggc gaaaacctgt atatggacaa ttggtacggt gcgggcttca gggaatgcga    16620
ggagaatacg cctggggcga tggtcatcat gcagattagc gcgcctgtgc caaaccacgc    16680
agggatattc cttccgggca accaactact acaccatatc tacggcagtc tgtcgagcgt    16740 agtcccttc cgggcaggat ttttccgcga caatgtggtt aaatgggtcc gtcataaaga    16800
cctaccgggg gatatcacaa aatggcaatg accacgttta aattgtacgg cgtcttaggg    16860
cgtcgttttg gtaaagtgca taagctggac tgcttcacac caggcgaagg actcaccggc    16920
ttgtgtgtga agctgcctgg gttacaagac ttttttaatgt ccgcccacct ggacaacatg    16980
atgttcaagg tgcgcaaagg cgaccacaca atgaccggct atgatgagct aggcgagttc    17040
cacggcaacc gcgtcgttac catcgcgccg gttatgactg gcgcaaaaag aggattgggg    17100
caattgctgg cgggtgtcgc gatcgtagtg gcgtcgttct atacgggcgg acttgctact    17160
gccgctttcg gggcttcggc tgcaaccgct gccgctatcg gtacggctac attttcgttt    17220
ggcatgtcgc ttgcgctggg cggtgctatg caattgctgt cgccgcagcc gaaaggattg    17280
cagacccggc aggacgtgga taacaaagcg tcgtatgcgt tcggcggccc tgtaaacacg    17340
accgcgcaag gtacgcgcct tggtgtatta tggggcgagc gtgagatcgg cggcgctatt    17400
atttcagccg gaatcgtaac cgaggatttg aacgaatgac gattgtctat gacgtcacag    17460
gccataaagg cggcggtggc aaacagcaca ccccacagga gacacccgat agcctgcatt    17520
cgctggctaa aatccgcatc ttgcttgcgc tgggagaagg tgagttcgaa ggtattccag    17580
accctaacga attacggcgg cgcgtatatc tggacggaac accgatccag aatgcagacc    17640
tgtctgaaaa cttcccaggc gcgcgtgtgg agttccgccc cggaacacag caccaggatg    17700
tgatccacgg attttcagcg gtggaaagtg agcaatctgt cggcgtaaaa ctggaaaacg    17760
gcacgccgtg ggtgcgccag attaacgaca ccagtttgga cgccgtgcgc attcgcatcg    17820
gcattccggc cctgtacaca aacgaagata atggcgacct ggtgggcggg cgcatcgact    17880
ataagatcgt tgtgtatacg gataacgcgg acccgcgtga gttcagattc gccgccgttg    17940
gtaaaacaat gtcgctatat gagcgtgacc accgcatcga gctaccgtcg aacgtgaata    18000
ccggttggcg cgtggaagtt caccgcacaa cggcagattc cacatcggcg aaagtggtga    18060
acgatattca ggtacaatca attactgaga ttatcgacgc ccgcctgcgt tacccgctaa    18120
ccgcgctgtt gtttgtggag ttcgacgcca aagcgttcca gaacatcccg cgcgtgtcca    18180
tcaagtgcaa aggccgcaaa gttctaatac cgaacaacta cgatccgatt aatcatacat    18240
attccgggga ctgggacggc acgtttaaac gcgcatggac ggataaccct gcgtggcact    18300
ggtacgatat ttgtattact gagcgcttcg gcctcggtcg gcgtatcaaa ccgcaaatgt    18360
taaaccggta cgcgctctac cagattgcgc agcgctgcga tcagttggtc agcgacggca    18420
acggcggtcg agaaatccgc tttaagaacg atatgtacat ccagtcgcag acagacgcct    18480
ggaccgtgct taaggattta gcagctatct ttgccggtat gacttggtgg ggaaaccaga    18540
tgttgaatat cgtaagtgac cagccggtcg cagcggtatc gcacactatc accaacgcct    18600
cggttattga tggcagattc gactacgcgt cagggagcca gaaaactcgc tattccactt    18660
```

```
tcgcggtagc atacggcaac ccgaaaaacc actacgacga tgccatcgca acgggacaac   18720
gtgtcgaact ggtacgccgc cataagatta accgtctgga tataacgcg atcggctgta    18780 cgcgtgaatc agaagcgcaa cgccgggggc actgggcgct aatctccaac cagcttgacc   18840
agcaagttag ctttaaggtt ggcatggagg gactattctt tattccgggt agcgtagtcg   18900
cgatcgccga tacaaacatt tctggtggct tcgagacacg cggcggtcgc ctgttgtcgg   18960
accctggcac gcgtaccgtg cttaacacgg acagcgaaat cacgttccgc ccaggagata   19020
aattcctggt acgcaccgat agcggtaatg tggagtctcg cgagattgcc agcgtcaacg   19080
gcaacaaggt tacgctaaaa accgcactgg atgccgaccc gattccagat caaccgtttt   19140
gcgtggatgg caacgatatc cagttgcaga aattccgcat caccgacctg gaatatgacg   19200
actctaccag cactttctcg gtgcgcggga tcgagtacaa cgatagtaaa tacgatgccg   19260
ttgataatgg cgctcgcctt gatccgggca tcttcacgca agttcctgac ggagtaatga   19320
aggggccgga gtccgtgacc attacgccgt cgcagatttc atcgcaaggc cagctaatca   19380
ccaacgtgga tattgtattc ccgccggtga aggatgccgt ggtgtatgaa atccagtggc   19440
gacgtaccag cttgcagaat atggcggtcc agtgggggaa tgactgggta acatcccac    19500 gtacggcatc taacggcgcg cacatcccga acgtgttttc cggtaactac caggcacgcg   19560
tccgcgcgat cggtatgggc gagatttcat ccccgtgggt gtcgtctgcc atcacaccga   19620
tcgaaggtcg tctcggcggg cttaacgcgc ctatcatcac caacgcgatt tcgggactcc   19680 accaaattt gtggaagtgg aaccacaaca acgccgcgac ggatatttcg tataccgagc    19740
ttgaagtacg caagctgggc gaaacggaat ggaagttctt gaccaacgtc ccatatccgg   19800
ggtcggacta tgcgcaaacg tcgctggagt tcggcatcta ccagcagttg cgcgcccgcg   19860
tagcggataa aatcggcaac ctgtcggact ggtccgcccc gtttgaaggc caggtgagtg   19920
acaaagttga cgagtacatg aaggggcttg atgacgcgtt cttgacttcc gaagatggta   19980
aacacttcca ggaagcaata gacaccattc cgcagggcat ttatgaatca atgctcacgg   20040
acgcccagca gctattcaat gcccgcgccg agtatcaagg tatttacgca gaaatcaagg   20100
tggcgtataa cgtggcagcg gatgcccaca aggcggtcgc acaacttgag acgctgatcg   20160
gcactcgcct tgacgatgcg gaagcggcga tccacacgtt gcagacagcg caaagcacgc   20220
atgaacaagc gttcgcccag taccagcaaa ctgttgccgc taagttcggt gaacaggaag   20280
ccgccatcga tcaggtacaa acggcaacgg cagacgtagc gggcgcactg gcggagtata   20340
agacccaggt cgcggcgcag ttcggtcagc agtccgcagc tatcgagcag aagatgacgt   20400
cctcgtttaa ccatgctggc ggtagcgcca catatagcct taaagctggc gtgacgtata   20460
acggaactta ttatgatgcc ggtatgcagc tttcagttgt ggcggaaggc ggcgcggtta   20520
aatcccgcat cgcgttcaag gcggaccagt tctacatcat gcacccgtcg aatgggtcgc   20580
tttcgtccgc gtttatcgtt gacggcggtc aggtgtacat cgacacggcg cgcatcaaga   20640
acgcgtccat caacttcgca cagatcacgg acacgctgca atcgaataac tggaatccgg   20700
ggagcagcgg ctggcgtatc gcgaaggatg gcggggcgga gttcaacaac gtcacggtcc   20760
gcggcaactt gtacgcgact acgggtaatt tcggattctc cggcgggtcc gttacgatcg   20820
actcaacggg cgttaacgtg ccattacctg gcggtggtag ggtgaaagta gggacgtggt   20880
aaatgcgaag gggccatctg gccccttct aatacatgtt agggatgact agtaacggtg    20940
tgggtacggt tacattacga ttaggcatct ggaattgctg ccgtgagtag ttaccgatca   21000
cgcgatttcg tgccgcgcta accacgttgc cagccatgcg tatcccgctc attcgcacgt   21060
```

```
ggttatatcc gctgttgttc tcaatgagcg cgccggtata tgagagctgt acgaggctgt    21120
tgccaatatt ctgaccacca gtgctgatat taattacgga attgaggaca aacggcttat    21180
tcacagtgga gaacgtgacc tggccctggt tgttagtcat agtaatgccg gtccccggtg    21240
atggcggcgt attgttgaat atcaccaggt ccatatccac cgaagccgcc acatcgtcaa    21300
taccgccata ggacgcattg cggacaataa tactgccgcc gtcgaagcct actgatacgt    21360
tgccatcgtc ccatcgggcg aacgggacac cgctaacggg caatgccata ctaccgttga    21420
cgcgcacgcg ctgtgcgtat cggcaggtca ttagcttaga cacgttggat atggcggtga    21480
agtccgtcga gttctccacc agtaagcccg cgttgcgtga accaaccggc agcacttcca    21540
ttatgacgcc agcccattgt ggtaagccag agtacgcgcc atacgcatcc tccccgcgca    21600
gggtgatacc actattcccg ttgcgggtaa cagacgtaac gtaaaacggg tcggaattca    21660
ccagggtctg gtcgaatacc tcaatcactt ctaccgggcg agtgagcgcg acgacgacct    21720
gcgacccctc cgtaagcggg gtgttaatgg ttagcgtctt gttggactgt gcccgctggt    21780
taaagctggt gcagtatgac ggcgcgcgga gtccagcggt tatctccatt acaggcctgc    21840
cgtcgttata gtcgataagt attccagcgc ccattattac cactcccgtg atttaactga    21900
tactgtgcct gagaagttgc cgtcgctatc ggatgacagc ccggtgaatc gcatgtccac    21960
atctcctgcc gggactttt gcccgtcaac gtagcgcaac atgcagctac cgtaagcaac    22020
cgtaacgcaa tcgccgttgt tgcgttctac ggcgcaaccg gacaacagaa ccgcacaaat    22080
cataattaaa gttttcatgg tatcatctcc tatatttggt tgagttttag tattacaccg    22140
ctcagccagg attgcaacca atttatgagg attcagctat ggcagcgggt acactatccg    22200
taacgaataa cagcaaggcg gttgccgggg taggcacgac gttcaccgcg tttaaagctg    22260
gcgacttctt aacgctggtg gtggggcaag tcccttacac tgtcgcgatt gcatccgtag    22320
aaagcgatac cgcgcttacg ctggtgcttc cgttcgacgg tcccacggca accggccttg    22380
cctgggatgg cgttgcgcgc gataccatgt cactggcgac gatgggcgtt accgtacagg    22440
cccagaaagc gttgcgattg atgatcgccg atgaaaacaa ctggcgtgcg atcttcggag    22500
acgaagaaga agttacggta acgctgccga acgggcaggt tatgcagggt atgtcgtggg    22560
gctacctgtc gcgattactg aaggaagttg accccgttga aatgcgcgac ctgcaacaac    22620
aagccgccgc atcggaagcc gccgcactag catcacgtaa cgaggctgaa ggattcaaga    22680
acgagacggc aggcattcgc gacgccaccg atcagattaa gacggatacg caggcaatcc    22740
acgacgccac caacgccatc aagacgcaaa ccaaccagat taagacagat actgcgcta    22800 ttcgcgacga ggccaaccag attaagacgg ataccggggt tattcgcgac gaggccaata    22860
ccgcgaagat tgacgcgcaa accgccagca ctgccgcgca gggatttcgc gatcaggccg    22920
aagaatgggc gcgaagcgta aacgccgata atctgctaac taaaaccggc aacctggcag    22980
gcattgcaga cgctgcggca gcgcgcacca atttaggctt aggtactgtc gccacgttaa    23040
acactgttcc tgtcgctaat ggcggtacag gtgcgaccac ggctgcagca gcgcgcacca    23100
atttaggctt aggtacgact caggttgtat ctttcgggtc agtggcgttg actaacgttg    23160
ttacgggcgc ttacgctagc ggttttgggg caaccgtagc tggcggcagt tttggggaac    23220
agtataccaa ccccacagca attgctgtag atagcaccgc tgtcgaaggt tacattacgt    23280
taatgagggt tacaataccc ggtgtgggta acccggtgg catggactgc ttcatgtacg    23340
ctaatggtac gtcgttcttc agaataaata ccggtgttgc aaattacgtg tttaacagta    23400
```

```
ctggggtagc caccgctaca cagtggtcga gtacatctga cgagcgaatc gaagaggata   23460
ttgcacggat tgataacccg ctcgaaaaaa tgaagcgtat caaaggtgtg tcatggcgac   23520
tgaagacaaa cggtagtatc ggtcacggtt tcatcgctca ggatgtggag caagatttcc   23580
ctagcgctgt caatccgtta caagatatgc aattgtccga cggtagtgtc gtaaaaaacg   23640
tcaagtctgt tgacacgtac ggcgtggccg cagctttgca tcatgaagct attctcgcac   23700
tcatggctaa aatagaagca ctggaggcca ccatgcgagc gttgccggat acgatgaaac   23760
aggtggagga gttgaaagcc gcacaagcgg gctttcgtaa tattcctttc cgtccacttc   23820
cactaagggc caatcgttaa caatcacgta cggctcagca atatcctcaa tcacgccgtg   23880
cgcgctatgt tgtccgaaat ctacgcccac caggataacc ccggcaacgc gacgagtgag   23940
atactcgcga gcgcaacgag cctctaccag tccgcgacgg atgccgctgg tggccttaac   24000
ctcataggtc cagacggcat caatcatgtg ttcccggaag tcgggccgg acttaacctt    24060
gcgcttaccg accatgataa tatcgccgcg gtcgatagtg ttagcactaa acaggccggt   24120
acgcattagc aaaccttgcg gtatgcaact acgcccgccc gcctgcccct caaggtacat   24180
gcccgcaaac atctcgccca gcacaccgac aagacggctt tgcttgcacg cgtcagactt   24240
taggcgccac tggtcaaact ctatgcttgc gatcattgcc gccaggtgga attgtttacc   24300
ggatatttca tattcgccgt acatcgtgtg gtcctcattg atgcgggccg aagcccgcga   24360
ttagaattat ttcagtgcgc tacgtaccag tgttttttcc atgttacgga aatcttccgg   24420
cgtcatgagg attttggacc catcttcgcc ggtgagcacg accataggct ggacttcttg   24480
gtctgcaatg ccgaaattgg cggcttttac agtcttaccc accgatgcag aaggattcca   24540
cgtccccgcg gtggcgatgg gccaacccttt aaggctgtcg tattgcgctg ccgttgtatc   24600
gacctgaatc tcatcatgta cggtcatgta agactcgccc agcagggcgg catacgccac   24660
cagatccacg atgttatctt cctggtgctt acggtgctgg cgcaccagct tcaggcagat   24720
caggaaggtc caggcttctt gctcggtaag gtcgcgaccg gtaagcgcgt taaacacggc   24780
agcgatttgt ttagcgctgc gttcttcttt cgcgttgtca tagccgtttt cttcccgcg    24840
ctgttccata gtggtggcgg cgttttttgca gtattcgtat gctttcacag tattgccctt   24900
tttagcgagg gggcggtaat gcccccgaca cgtttactat agtgcaacca acctattggt   24960
tgcaagtgaa tttcgcaaca tttatcgcgt aaattttcgg gaccaaatca ccacacgccc   25020
gacgaattgc cgcgatgttc ttctcgcaat cttcaatgat gaccagttcc gacacgtccg   25080
catagcagac catttttgaac acggcgcacg ccttaaactc aggcggcggg gtgtcgtcca   25140
gcatgtggcg cataaacaac cggcctaccg ggaagacctc caattgctcg gcggtggtgt   25200
cccagcattc gcgctgccgg ttggtcagat acgcgatctc gaagccttgc tctttataca   25260
tgcgcagtag cggcagcata tccatgttca ggtcttcgcg gacgtgcgcc ttgtgccact   25320
tcgcccagaa ggtggattta gttttttatgc ccggcaccag gtcggcgcgc gcatcgcttg   25380
acccattaat aacgccatcc agatcacaaa tcagtaattt catttcaatt cctcaataag   25440
ggtgtatcgg gcgctgcgcg cggtgtaaga gttgcacacg aaatgacaac gtcgggtaat   25500
gacaagccac ccggtaaggt ccatacccag gaggtgttca ggccgtgaca cgcgacgcac   25560
acgatcgcgg cgcgggtcaa tgttatagtc tttttgcatt tggtctacga ccgcgtggtc   25620
gcggtcaacg attaagatat tcatgtagct cactctcgct cattatttca atttgtgcgc   25680
tgccgctggg cggcgcttcg tcaaagatta tcaactgctg gcacttgtta ttgctcggcc   25740
cgacttcacc ggttacagcg tgtataaatc ggatacgcca gtccagaaga attatcaggt   25800
```

```
ttgcagtctt ccgggccagc tttgcccact tcgtcgacgt gtcctgattc agcagcatga   25860
cggtccggcg tccgtgcgct gcgcacttga cccacggcag cggatcggaa tacggcgggt   25920
tgcaccactt ccacccttc aactcagacc agtccgcatc gagcgcgctg tgctctgccg    25980
tgaagtaacg cggtagcagg tggttggtgt cgcttgccgc catatcgtaa cggaatcggt   26040
acttacggcg cagcggttta aataaagctg gcggcgtgcg ccagctatct ttttgctcac   26100
tcttctgcat gatctggatc tatcgcgtac agggcaattt tcttattact gtttagaacg    26160
cgttgcacgc gctttgattc ctcggtgccg agtggtcggc agtcggagta gtaagacccg    26220
ttccctcgcc acgcaaccag caccaggtct ttccggtcaa tcttagactg gcggcccttc    26280
ggacgcacgt actcctcggc ccgtttgcaa tgttcacgca aaccatcggc agtgatgcgg    26340
tttagtgcaa cgctggtggt gtatccggtg cgctgcataa tccccatcaa ttcgaatagc    26400
agttcgaagc gctcctctag ctcctggcgc actttcttct cccttcata tagcgtctgg     26460
ttggtgtccg ccaacgcgtt cgcacgttcg gcctgttcgc gggcttcgag gcattgcgcg    26520
gcccagtagt tttctcttc ttgtaaaatt ttcatttatt taagctccgt tgtgcgaatc     26580
tcatcgcgag gaataaattt gccatccatt tcaacccagc agacaccgta tcgccattgt    26640
gtgttacggc ctgtttgctc ggggtacaca gcctcgcatt cgtagcgttc cgtgtagtaa    26700
acagctgcgg taggtacgca aacacaaacg gcaatcatga gggtgaggag cacccaaaat    26760
ctaaggtcgc cgtcgtagtc gaaaaataat gatttcatct caccgtctcc aggtattaaa    26820
aagggcgtcc aaccggacac cctcaatata atgcaaccaa tataattacg caaccaattt    26880
acgcataaaa atttgggtcg cgcgctacgt ctaccagata caggttacta atgcggttgc    26940
cgtagtgccc aggcgtgcgc tggcggcaca caacggcgaa tcctgggggg attgtattgc    27000
ctgtctcaat aatccacgcc acgcgcgcgc ccgacagcgt cttgccgttg cactcgatgc    27060
gcgtgccgcc atcggcagtg ttaaggttgc caatcttgca gcctgtggac ttcaggcgaa    27120
tgacgccggt cttgctgtcg taggaaaaaa gctgattggt cattgccact gaaaagtcga    27180
tggcttcgaa tgtagtattc atttaaatt ttcctcgtta accgctatcg cgaagccgcg      27240
cggggtgagt gagtggatta attttgtacg agcggattta ccaccgaggc gactatactg    27300
cttcgagtac cctttttcaa tgaaaacagg tttcttctct ggcatacgga agccgttgcc    27360
ggtccataag caggtcagct tcggatatga atcgcgggcg ttgatgtatt ccggaagag     27420
cgggtgtacg tcatcctccg gcagatatcc cccatactcc cacgggttga atgagtgatc    27480
cggcttgcgc cactgggtgg aaagcacact gcgcggattc tcaatcatat atggcacttc    27540
gaagaagtca cccaggtaag cggcgatctt cgcggtgcgc accgccttaa gctgaaaggc    27600
tgggtcttta gcccgcttgc gcgggaaagc tggcgcaccg ctcactgcca gatccgtaca    27660
cggagggaat gcatagatga tatccggcgt accgaaatcg ccattcatcg cgcggtctac    27720
aaagtccaga tcgataaact cattgcgata ccggattccg cgaccataaa tccgtagtc     27780
aaggtaagac ccgtgatcgg cttcggagta gttgaagcaa taacacttat gccccatctc    27840
ggcagcacgc tcaatcatca agccgctgcc gtcaaacaac gaccagattg tcattttagc    27900
aatagtcatt tgcgcgcctt tttagctttc atgtattcca tcaggtcgtc ctggatatct    27960
cgcttactgt cgcgacgctc ggcgaccaat tcatccagtg tcccgcgcgc ctggataatg    28020
tagacgaata ccggtcgagg gtgtccggcc tgcatctggc gaaccggccc gatacgttca    28080
acgatctgcg aaaagtgctc aaagttccag gtatcggaga agattgccag gtgatgtccg    28140
```

```
ccgtcctgca agttaaggcc gtggcctgcc gatgccgggt gtgcaaacat gatggggatc    28200
tcgcccctgt tccacgcttc catatcctta ttgccctgct taccttacc caacgcaacg     28260 ccgtgcggaa atttcttctt aagacgtgcc aggtcatgct tatactgata cgcaacgagc    28320
aacggcgcgc cgttcaactc ctccacgata cttttccagcg cgtccagttt ggcgtcgtga   28380
atcttcaccc actcgtcggt ccgttcgccg tcttcgtcca ccttatacac agcgccggaa    28440
gcaagctgaa ggcacttaat tgtcttcgat gccgcgttcg ccgcttccac tgttccgctt    28500
tccagttcgg caaatagctc gctttcaaac tggtcgtaaa tcttgcgggc tttcttcggc    28560
aggtccacaa caaccggcgt atagattggc ttgtcgcacc cgaagtattc agccgcgtca    28620
acggtgaggg atacatctga cagacgttgt tgtatctctt tctcggagtt ctttagcgga    28680
gcgtgctgca tagtgaagct gccaggctta acaggcttgc taatgaacca gcggtcggta    28740
aatgccttat agctactgcc gaggcgttcg cctccgtcga caaaccacgt ctgacccat    28800 aagtctttaa gcccgtttgg cgctggtgtg ccggtaaggt taatccagcg cttgacgtgt    28860
ttatgtgcaa tcgccgccag tgcgcgggcg cgcttgctcc cctgcttgct acgatagcct    28920
ttcagcttag tcgattcatc ggcaacaacg accgtaaagg ccacgcatc gccgtaatag     28980 tcgaccagcc actcaaccac atcgtagtta acacaaacca cgttagcgtc gctctccagc    29040
gctgcaatac ggtccttctc cggcccggtg ccgtctacga ccagcaggga tgagaaccgc    29100
catttctcct gttccggggg ccaggtgccg gatgcaacgc gcagcggggc cagcaccagt    29160
acgcggtcct cctggtttga caggatgcca gtctggaaca ttttattcag cgcccacatt    29220
gtcgcgccag ttttaccgga tcccattgtc gcccatatat tgcatcgctt atgcttgagg    29280
atgaacgcgg ttatcaactt ctgatattcg cggcgtcgga atcttgccat gtcttattc     29340 cgcctttttc cagacttctg tctcactgtt ccagttcctt tttgtggcgt cgtagttggt    29400
ggcgtgtccg atgtggacac cggtagcccg gaagctctta aatttttgcc agcacaccgt    29460
caacggcagc ggatcattca tgcctgcgat aaaccatacg cgatcgcccg gtttacattc    29520
gcccagcttg gttagtcggt aatgttcttt catcgtcatg tctcccaaaa atggcgggac    29580
aagcccgccg tattaattat ttttgttctg cacggtagcg gcgctgccgt tcacgctctt    29640
tcttattgcg gcatgatttg cactcggccc gatacccgtc cgggctgcgc gcagtcttgc    29700
cagtgtattt gtggaactgg gatagcggtt taacgcagcc gcaattacta caacgttttt    29760
cttcaatcat ctctaaaatc ctcgatatgg ctaaccggca cactataccg ctatgcgacc    29820
aattcagcaa ccaataaatc gcagtcggat atgttgtcga taacgcgaac gtcagcaccg    29880
cggcgggcca ttcgctcatg ttcacgtacc tggtgcggct tcggttttcc tccggggcgc    29940
ttcacttcga cgaaaactat cttgccgttg atgatgataa tcagatcggg cgcacccgag    30000
cgcccctccc atgccacttt gcggcagaat ccgccgacgg cttccacccg tctcatcaag    30060
tgactttgaa tcttgccttc tggtgtcatt atttcctgta cctgtacata atgtcgcctt    30120
ccgctgcaag cgggaagcct ttcgcccaaa ccggcaggtc gcacatcagc gcgcacaact    30180
cctcggttgt gtagtcgtcg gtatccggca cttcggttat cagttcatcg tgtacggaca    30240
gtacgatctc atatcccgca gcttcaacgc caggcatgga ccatgcgagg atatcgcgac    30300
acagcgcctg cacgatgttt tccgtgagtt tgccgccgta ggtgtactgg aatccccact    30360
ggcgcgtcgt ctgattctca ccctgatatt taatgcgggt gctggtgcgc ttcttgccgg    30420
tgtcttcgtc gatctcggtc gtgacagaca gcgcgatgcc ggggtagctc atgatgcgcc    30480
ccgacggtaa ctcaatttc aaccaccacc ccgcggcgtt cggaccgtcg cgctcctcgt      30540
```

```
cgaaggttgg gtcatgcttc gccttcgtgc ggactatctt gagcgctttc ttaccatccg    30600
ggcgaacgtt cgcgccagcc cagtacgctt tgcccggatt gcggatcgcg cagagcaccg    30660
cgtcttccag ttcggcccaa aatgctaccg tcttcgggtg cgactcacgc cacatacgtt    30720
tgatcgcatc acacgtcagc catacgtttt tcggcagtat ataagttggg cgctcgtctt    30780
tcttgccagg cttcggcggg cgcttagctt cgttaatgcg ggcgtattca tatccacgtt    30840
tcgctgctgc ccaaatgtga tcggggaatg tgcccttcat gacgtccgcc atcgcgtaaa    30900
ggtcgaggcc caggttttta gcgaactgca agaacgcggc aacgccacct ccatagccca    30960
accccaattc gcacgcctta ccaatctggc gcaagtcttt gcggttggct ttaatgtatt    31020
ccgggtcgag gccgaacatt ttaccggcag tctcacaata aatatcgcga ccggccctaa    31080
ataccattag cgcggttttc tcgccagcga tccaggcgag gccgcgccct tccacgttgg    31140
agtagtccgc tacgacaaac ttcttgccct tcgccggaat aatgcacccg cgaacggtcg    31200
aggccgttag cttcgatatg tcatatgccc agtgcgctgt cccgcgtaac agggagttga    31260
tgccgttggt gagcatgtgc gaccgcaccc aaaaggatat atcgctctcg ccttcacggc    31320
gtttaatctt cccttcgtgg tcgtcgctat actcgccgcg tgccaggttt tgaggctgga    31380
atcctttacc ggcccagcgt agcgtgcgct ttgcgccacc atactgaaga cacccacggc    31440
ggcgaccatc ggcggatagg ccgttaacga gcggattgta cttagtcgat gccgttgatg    31500
acgcaccgag gcgcatttcg ataagcgctt tgccttcgtc ggggaaatcc gggtcttcaa    31560
gcaggtcgtt aagtgtggat ttctgcgcgt tgtggatcgt gaacgccggg gcgatatcac    31620
gcaggattgg caggaagtca ttgccggtca gcttaccgcc aaatcgctcc caggcttctt    31680
ccttcaattc ttccttatgc gcctgcaccg ctttgatcgc ggcgttcgcc aggtcaacgt    31740
ccacatagaa gccgcggtcg ttgatcaact ggtcgatatg taggatttca tcttccttcg    31800
gagtattacc ccagtccggt atgcgccagt agacttcacg cattgcgata atatccagcg    31860
cggcatagcg cagaaatttg gcccattctt ccgggtgagt ctcgcgagtg tagcggcgta    31920
ttttgtaggt cttaggggta ggcttacaga atcgtttaat cagcgccttg cctgccttat    31980
ccttcgcgtg ctctgcgtca acgcccagca cctggcactg catatcgagg ctacccggca    32040
gcgcgtggcg aaaggccata atcatggtgt cttcgatctg gcttaccggc aggtcgatgc    32100
cccacttctc acggataacc aggcggtcaa acaggaggcc gttagccatc actatttttg    32160 cttttcttgcg ggatacatgg cggagcgcct tgcgcagttc acgcggcatt gtgggggatt    32220
cagtgcaatc ccatgtctgc acgcggcctt cgtcgatggc gtaggtgcaa atcataatct    32280
cggtagttgg gtgttccgcg taggcgtatg cgcccacttt cttcagatcc accccgctaa    32340
atgtctcggt atcgaggaaa agtcgttcga agtctttcat tgcttaatcc tcactacggc    32400
gtcagcgctg ccgatcatag agaagatacc gtcggaaagg gttatctcct cgccgttgtt    32460
gcgaacctcg gcaacggtga aatattcccc cagcaatttg gaccatacct gcattccgac    32520
ttttacttcg ctggctttaa tgcgcatttt tcattgtcct attaaaaagc ccgcactaag    32580
cgggcttgaa tagtgggctt tgcccttaac ggcggcgacg tttacgcggt gctttgtctt    32640
cgtcgtcgtc gtcctcatct tcgtcatcgc gtggcttacg acgttacga ggttttttat    32700 cttcatcatc gtcatcgcga cgttttgact ttttggactt gcgcggcttg tcatcttcat    32760
catcgtcgcc caggtcctcg tctgagcaag aagacccgcc acctccgaag gcttcgccgt    32820
cttcacggaa tcgcagaccc agcaagccag ccccgaggcc cttgccgttg gtattgttcc    32880
```

-continued

```
atgcccaaat atcaagggac acgttgcaat aacaaccgga gtagatctcc tggccttcaa    32940
tctcgtcgcc ttctacggtc agaccttgtt cagtctgctt ctcgccgagt gacgtttgaa    33000
tgataggctg tttgaacgat ttggcgttga tatacaacat gccttcgaat tcttctgtca    33060
cttcgtcgcg ctcgtcaccg tcgcgaactg cgcattcctt agaatcctgg gcgtagtggc    33120
ggtccatcca cttatcggca ttcttctcgg atttcagctt atcggtgagc actgcgcgcg    33180
ctgccgcttc cactttgtcc acctgcggat cttctttatc cagaagaatc acggcacggt    33240
atgccggttt ttgtccatcc tgtttagggg tatcacgttc ccagattttc aggaagcata    33300
cgcgcacatt tttcaggttg actttagcca ttttccaatt cctcattttc acatgtatcg    33360
gggttattgg aagccacccc gttcggcttg gttgctaatc tacttggttg cgcctgagcg    33420
gtcaagcatt tcgttaaaa agatttcggg taacgtagtt ggtagcgtta tcgatccagc    33480
ttaacggcgg gcggtcgatg ttcttcttca cccagtcgac ggcagcgtca ctatacccgt    33540
catcaagcca gcgggttgga tggcgaatca tccacgccac cattaacacg ccttgcacgc    33600
aatgcaggat aaagcccagc gcgccgagca aaaacatcaa taagattgcg aatactttat    33660
tcattgctta agtcctcgtc agtagcttcc gaccacgcag ggcgcgggtc gtcgattggg    33720
gctaacaccg gtttggcagg tgcgcgcgtg attttatcac acagcttagc ccacactttc    33780
ggttttcgt ccttcagtac cttctcggca tccgtagggc tgagcaatgt ttctttgtac    33840
atcacatcgc gcttgatccg ggccttcgtg aagatttcaa tcacttcgct ctcgtccgcc    33900
cacttgcgga tcccttcctt accggcaacc atcttgaggc ccagcgattc gccgtcgccc    33960
gccattaccg ccttaaatac cgcggactcg atagctttga tgtgctggcg cattgcgtcc    34020
aggccttcat aagccttgcg cagttcagcc gcgctcatag cgccggggc cgcttctttc    34080
ttgccacgct tcgcacgtcg cgccgccttc ctggcttcac gcgccatatt gcgatcgtgg    34140
ttggcgcatt cttcctcggt cgcaataatc acgtcgtcgc ccaggtcttc gtcagttgcc    34200
gtggttggtg tcatcgtatc gattgcggcc ttcgcgcggg cactacactg atccgcaaat    34260
cggcaccact gacacgcatc aacgctgggc cggaagtctg cgcgagtgag tcccttcttg    34320
cctcgggaat atgcctccag tgcggaaata gcgcgcttgg atgcaaactt cgcgaatatc    34380
tccagtgctt ctaccgaaat atcccactcc gacgccccgc cgcaatacgg ctggaagata    34440
accaggcgaa cggtcgtaat gtcgtacata gtttgcagct tgcgcagcag gccgagcgcg    34500
tacaacataa gctgtttgtt ctctttcgcc tcgaccttat gccgcccggt cttcaggtcg    34560
ccaacaatca gcatgtacgt tccatcggtc tttttcatga ccatgaccat atcggcagta    34620
ccgaacgttt taatccggtt gccgtcgatc tcgtagcctg agtgaaggac gcgggtcaga    34680
tcggcgcgca tctcaagctg acaaactcc gccacctcga ggagtggtcg ccagtggtcg    34740
atgtacgcgt cgcactgttt caccatgtcg tcattgacca gtacgccgcc tttcggcgct    34800
ttcggatgtg ccttcactgg ccccttgcct tcgttctcga cgtagctccc tttatacgtc    34860
tttgcggtta tcagcttttc accggcgata atgcggttta gcaccacttc cgatacggtg    34920
tgcatactcg taccgttaat cgcggcttgc ccggattcgt tcgggatatc tttttctacc    34980
accagggcgg cagggcaacc catccatttt ttagcaccgg atggcccgag taatgagtgt    35040
tccgtattgc tgccggattg cgtcttacgt tttggtttaa tcgccattat tccacccttg    35100
aaaactgagc aatgtaatat tcatgtttaa cccagcccg cttcgcggct tcgttcatgg    35160
tagccgccaa acctctggct tgagtccagc agcaattcca gttctgattc ataacgattt    35220
ccggttgctc atcgccggta atacggcaac gaaataaaac aaagaatata gccatttatt    35280
```

```
ttgtctccca gcggtcaatt gttttgctt cggatgcaac tgcgaagcga acatattcca   35340
gattggaatc cgcccaaata taaaagtcgg ggttagtaaa ggtggtgcgc ttaatttgcg   35400
cgggggtgtt acggcgttta tctattacgg caacgcgtga ctgaaagctg ccgatgcgtt   35460
cgaatagcca atagtacggg cgctggtcgc gggagtccac cgcctcgatt agcgtgaagc   35520
gtgccattgt ctcgtcctct aaaaagaggc ccgcagatta gcgggccgga taatattaat   35580
cttccagttc gaaataagtt tcgacgattt ctttaagttc tgtgtggaag tcttcgacgt   35640
cttcatcttc cagcttggcg attgatttga tctcgaacga ttccagcagg tcgtcaaatt   35700
cgtcgttcgc gtcgtcgtcg tcaccaccag cgataatagc ggcatattgt ttgatttcgt   35760
cgcgcatctc agccagcgga tcggcatctt tcttgccttt gcctttcgcc ggggcttttt   35820
tacccttagc tggttttacg tcatcagcgt catcgtcgtc gtcatcttct acgacttctt   35880
ttttggcttt cgccggagct tcgtcgtcag cgtcgtcatc ttctacgact tctttttcg   35940 ccttagacgg cttcttgtct tcctgcttgc caacggcagc gccaacggtt tcataatgct   36000
tagcgatggt ttccagtgct actacgccgc gagtaatcag gtttacgatt tgttcaaaca   36060
tgttttatat ctccgattgg ttaagtttag gtgtcgacca ttaacctcgt cggtggcctt   36120
aacatagtgc ctggttacgc gttctcccgt tcgggtagtg gaccaggtta tataatcacg   36180
gttgggaatc ctgacacttc gatccggccc ctgcgttgcc cctctccagt ttgcgtcctg   36240
catcctgtcg acggagtgaa tattagattg gttgcagaat ggagtcaaca actaatttca   36300
aaaaaaaaag cgccgaggca aaatgcgacg gcgctaacca ataagagaca atgagacggg   36360
aattattatt acacgcgtgc gcgcccgttt caatatatca aaggagttga caccctgctg   36420
ttttaggtgt agtttcgttg gtcattaacc aaccggggac agaaaaatga atatcaacga   36480
cgcaatcgaa atgttaacta agactgtttg cagtgaaaca agccggtcct gggcgtatac   36540
cgatgccgtg ggggcggtgc tatttgaaat cgaacgcctg cgactcaccg aaaaagaatt   36600
gcgcgcgaag ctggaattac tcaacggtac ggcagccagc aagctgcaaa agcacaatga   36660
agaaatggaa gaatacaaaa agcaggttat ccgtctacgt gaggaaggta atcctgggc    36720 tatgatcgcc gagctaaccg gaatcaacca gagcactgtg cgctcctggg tacgcaataa   36780
taaaacttcc aaataaggct acgaccatga gtttaattaa attcgccgta acaagacccg   36840
ctaaaaaagg cgaaaagcc agggcggaaa acctccagat gaccaccgat gaattttcg    36900 aatttatcaa agatgcgaaa gaaatctcat cggtgcatat caacaagacg gaggataaag   36960
ccgagtatgc gcgccgcaag cgtaaggcg atggcatcgt ggcatatacc agtgacggac    37020
ttcgccgcaa gaccagtgcg gtggaccgct cgatcctgtt ctttgatatt gaccgcaccg   37080
acacccgcac cctacgccgc tgccgtaagg cgttcattga cgcgggtctg gaacacgtat   37140
ttcacaccac aaccggcgac cgtcacccac tgaaaggcgg cacgcgttgc gcccgttcc    37200 tggtgttaac tgacaagcct gtaccggcgg aagacctggg ccgcgcccag tatgccttgt   37260
tagcccaact gggtctgtcc gatgtggact tcgacgattg cacgaaagac acaaaccgcc   37320
ttatgtacct gccacaccag caatctgtca ttaaatgcca ctacggcaag cgcgcccgcg   37380
tccgtcgtct gctccgcctg gcggacaggc tgggagttga aaagaggaa gtgcgccgcg    37440 aactaaccca gggtgatgac ggcatggcgg acggtattct ggattggtgc ttccaggcag   37500
gattcgaacc gctgtcgtcc ggtcgtggtt atgaagttcc atgccgaac gaacatctgc    37560 atagtggcga agggtccacc gctatcatgg ttaaggatgg cgagatccgt ttcaagtgta   37620
```

-continued

```
tgcacaccgg caacgagtgt tgctcggaac tgaatagaca ccagcacctg gcgctacgtc   37680
tcatcgggat accggaccac ctgaacgtcg agccgcacaa catgtcccgt aagcaaatcg   37740
ccgccatcct cccagggctg gacgacgagg aagtcgaatc cttatatgaa catattgttg   37800
atgcggttgg cgacggcgaa gaatacgcg tgtgcaccga tgcggatctg gataacgagc    37860
cggttgcgct gttcagcaag cacgacccga ttatcgaggg gttgattaac tttaaatcaa   37920
cttggtatat ggctggcgag tcgaacatcg gtaagtcttt ctacgtgctg ggcaaatgg    37980
gtgcggttgc cgcggggatt ccgttcggtg gcgcgaaggt agtccagtct cattgcttct   38040
atttcgatgc ggaaggtggc gaagcctcta accagcgtaa ggaagcattg cagatcaaat   38100
atgagcacga tctcgacaag ctgcacatta tcgacctgca aactcgcggc tgggatatca   38160
ccagcaaatc cggcttgcgt gaagttatca gctttatcaa ccgcaccgct aacgcgaac    38220
cggttggcct ggtggcattc gactccctca accagactgt tgcgttgcgg tccgccgatt   38280
ctaaaccgtt cgacgagaac aacgccagcg atatgggcga agtggtcaaa gcgctgaagg   38340
ccattgcgga aaatacaggc ggcagtgcgg gcgtcatcca ccaccgqcg aaaggtgcaa    38400
acggcagcag atctccccgt gggtccggcg cgctgcatgg tgctgtcgat tccgcgttct   38460
tcctggaaca gccggacgac aatcagcctg gtcaattgaa cctgtatcac gaaaaggcac   38520
gtaacggcat caagcaagcg ccgcgcggct tcgtcctgct caagtgcaaa gttaaggtag   38580
atctccgcaa gtccgaggcg ttcgaatcgc accagtccac cagcaccggg cctgacttcg   38640
gcgatgtggt tgccggttgg gacgtcaagc cgatcgcatc cacgccacgc gacgagactc   38700
tgtatctcgt accggtcgcc ctggcaccgt tcgccatcga acaggcgaag gcggcgggca   38760
aagcagcagt taaggacgag aatgccgcag gaccgcgcaa cgaaaaagag aaagtgcttt   38820
atgcggcgct ggaaaaactg atggaagata acccggacca taccggattc agtaaatcgg   38880
caatcgtccg ccaggcggga ttggcaaaag gtggcacatc gacgaaggca atagacgata   38940
tggtggagcg cggcgtgcta ggttttatta cagatccgca taccgggggcc atctatgggt   39000
cgtcgaatat cgtcataaaa acgaatatac ccatcacgct ttcggcgacc gatgacgacc   39060
ttaaagatta aattttgcgc gcattggttg ccatttttggg tgttttttat cggtcgtatt   39120
ggttgccgtg tagtgtagat ataatgaata gttatgcaat aaaactgcat aaaccaaacg   39180
ggacagaaag cgggacaaac aagggggcggg acaaagcggg acagcacccc cgtcccgccc   39240
cggatggcgc ggcctggaga ggagcgggac agcgggacag caccccagtc tttcagacta   39300
gacggggtc agcggccccc ctcgtctgag actgcataaa atccgggatt gcaaaataca    39360
cggcagcatg ttgcggattg cggtcgtcgc tgaactaggc aaccaatgcg agatgcggaa   39420
tggtgggtgg aaaatgcagt ttgcagtcac agcagatagc gatcaactt ttcatgcgcg     39480
tgattaatat tggttgcatt caatccggca cccggctata ttggttgcac accaacatga   39540
ggactgaaca atgagagcgt taatctggaa ttacacaatg gcagtggcaa acaggtcga    39600
agcgagatat accaacggca gagcaccgtg ggagcgcctg gtagctccga cctggtttgc   39660
gatcatggat gcgaccgcgg gcatggaaga ccccgagccg ttgcgcgcgg ctatcagggc   39720
ttacgcgctt gcatttgccc gtgaacgcct ggcctatcgc ttcggtattg gcgataaggc   39780
agtgacaaac gtcgcccgga ttaaagccca gcgcgaacta ttctcccagc ttgcgaaata   39840
aggggccaaa atgagccgta ggcgcgctaa acagctttcc tggcatattc ccctgcattg   39900
catacgaata tgggctaaga atgcgaatgt gggcgattct gtattctggt gttatcgcga   39960
tgacgttaag ccgttgtcgc agactcgcta cctgcaccag ttcgcagcac aacacgattt   40020
```

```
cagggtgcgg acctccttgc aaccaatggg gattcgtatt acattacgcc ggaagcccgc    40080
cgttgagcgg gtaggcaaac actggagact gagcaaatga tgattcgact aagcgaccag    40140
gtgacggact ccgagcttgc ggagtggatt gccgaagggt gggtcagtta tcgttacggg    40200
ccgcaggtat gggctattaa gcgctgccgt tgtgatatgc gcccgcataa cgtgcgcaag    40260
tttatacgca agcatggggt atttctggag gccgagaaat gttactaggc gacttcccgc    40320
aggagcttat ggacctgcat atgtgcgtac ttgaatacga acagaacggc attgctacgg    40380
tatgcgatgg cgacacgaag actatcgacg agattgagga gactgaacta tgaaattact    40440
attccgccgt aaagctgacg gtcgcatcct gaagccgatc cagaccctgg attcatacgt    40500
ccgcttacaa aacgcggcag gcaatcgggt atggtgggcg aagaaagaca agctgcagga    40560
agactgcgat attctcacac acgatattga gcgcggcgat gtgctgcgtg atattcgcga    40620
cggtagtatg tggatcgtcg aatatgtcgg tcttcatggc ctgcgtatgc aaaaccgcaa    40680
ggatggcgta ccggtatga cttacttcgg ccttatcaac tacgaacgag tgggccgcaa    40740
atacagcctt cgggatcgcc agccgcatga gcgggcgagc gccatagcgg acgcagttaa    40800
ccgcgtaacg catgacgtgg cgcagaagac gcgtgtagat tcacccgct acgactccca    40860 ccaggtgcaa gcgaagatgg gccgcgccgt acaccaaatc gtcaatcgct tcgatgccgt    40920
gacgaatgca cagcgccatg cgcaggaata cggttttgga ttcatccggg tagaacgcga    40980
cggcagcatg aaagccatcg acccgcgctc ggtgattctg agatgagtgc gacgatccga    41040
gatatgcttc agcataaccg ctttgagata ggcggtcggg tatttcgcaa ttacttcgtg    41100
gcgcgtgcat gggcgcgcca tattggcaaa ccggaagggg caattcgatg ttacacgatg    41160
tgatttattg gtttggtttg atctgggggc tgtgcctgct tactgcggtg ctgttggtcg    41220
tcctgttatt cgtagtatgg cccgccgtgg aagccgccag cattacccgc atgacgttcg    41280
agatctacaa gcgccgtgga atcacggagc acccgacccg gcttcggatg tggtggctgt    41340
ggtatcggga tatgataggc ggtcgaacat ttgaagccgt ccgatcatcc gggtgggagt    41400
ggaaaggcgt cggcaagtgg tccattttcg attaattatg caagcgtgat atagtcccag    41460
tgagctaaaa cttactggga ctttttttatg gataagctaa acgagtggtt attcgccatt    41520
gcgtgtcttg ctggtggctt cgtaggcgca cgcattcatg gcgaggcaac gaaagggccg    41580
ttgaacttcg ttttatatgt cgtagttgga ttcctgtgcg ccatatttgg tgcgccagct    41640
atcgccgagt gggctggttt atctggcgag cgcactgtcg ccggtttggg cttcgtaact    41700
gctatcttct ggatgccaat agccgcccgg atcaggagaa ctattgagtc gttccgactt    41760 ccgggggggcg caaaatgatt atctccgtcc tgttgtttgt tatcataggg gcttcgtccc    41820
tgtttaacgt gtatgcgccg tccgtccagg atggcttctt cggtcgggtg ttatatctgc    41880
taacggcaat gacctgtatt gtcggtctgt tgcaaacagg agacgtatct gacaccacct    41940
ggaccgcgtt aatctggttg tttgcattgc gcacgctgcg taatgctgtt ttgaatgggg    42000
taaaacatgc gattcagtga caacggtcta cgatttacgg cagcatggga gactttcatc    42060
ccggtgccgt atttcgcgac caagaaagag caggcccgcg gcctgtacac ctggggctat    42120
ggtcatactg gcactaatcc gcctcgaagc attacccgtg cggaagcgct ggaactgctc    42180
aagcgtgatg tggcgtatgc cgaggactgg gtgaacaaat acgcgcataa gagcattaac    42240
caggcgcaat cgacgcgct ggtggacctg gtaatcaacg ctggccctgg tccgatcgta    42300
ccggatgacg tcgcgaatga tttcgatgat gcggtgcggt tgggcgactg ggcgaaggtc    42360
```

```
cgtgctacgc tgccgctatt ccgcaagcaa ggcggggaag tgcttaaggg tcttgtgcgc   42420
cgtgcaatcg gcagacaggc gttatttgat ggtaagcagt gggacgttgc cgagcgaatc   42480
ggtcgtaacg cagcataata cgaggtgaca cagtatgtta aaaagtattc ttgatcataa   42540
tgcggacgcg cttgccgcac tggctaaaac cgaagatcct ggcgcacgcg ctatcatcgc   42600
ggacactatc agccacgcgg gggtcttcga tgcgaagctg ccaagcccgc caccaccgga   42660
agaaccaggc cccgcagcat aaaaccacaa gcccggttaa ttccgggctt tttattgctt   42720
tacttgcaac caactatcag actatactgc gaccaatcaa cgagaggagt aatactatgg   42780
aacctgaatt aatctgcatg gtcatctgtc atgaatctgc tacgcgcgcc gtaatcacgt   42840
atctggaata tggtgttttc ctgattgacg ataagtatta cgttatgaat gagcacggga   42900
actggactga agtattcaag tttagcgata cgcgcggtgt atggataact atcgacggca   42960
taagcgccgc tttcactgag attgagttac actatggcac gtaaagatat ttgggtatta   43020
gcgatctgga ccaccgcggc ttttatcggc atggttattt gcgaattgat atagcccgcc   43080
gccatacgga ccgtggtata ttgtccacgg tccactaatc aggaattaat taaatatgca   43140
cccgcaaact aaaattaccg atgagcaatt gatcgcagaa atccaggcag ggactacagt   43200
taaagagatt gcgaagaaat acgggattgc cctacgcaat gtctatatgc gtaaagcccg   43260
cctgtcgaaa aaaggcattg gacacggcaa cgatgccgta atccgcaagc gcgttgccga   43320
cggctttggg gttaagcgcg tatcggccct ggtgcgcggc aatggtgaag aggtcatgtc   43380
gtgggtcatc actgagcagg acaaagagcg ccaactcgaa gccatgcgcg ctgttgtcga   43440
tggtatgaac agcgaaatca caccggcagc gccagtaaaa gccccgccag taccgatcca   43500
ggcgctcgac ttgctcaacc tgtatactgt gtcagacttc cacctgggca tgttggcatg   43560
gggtgaggag actggcgaag actgggatat ggcgatcgcc gaagacctgt tctaccgctg   43620
gtttgtcgaa gccttcgcac gcgccccgga cgcaggcact gccgtaatta atattctcgg   43680
tgatatggcg cactttgata gcctcgatgc tgtcactccg gcaagtggtc acatactgga   43740
cgctgacacc cgctaccaga aactggtccg atacatgatt cgcatggtgc gcaacgtagt   43800
agaactggcg ctgcaaaaac accacaaagt aaaactgcta atcgtccagg gaaatcatga   43860
cgagtcgggt atgatttggc tggcggagat gttcaatact ctgtacgaga acgagccgcg   43920
cgtcgatgtg gatacgtccc cggacgtcta caaaatggtg cagcacggca agaccacgct   43980
attcttccac cacgggcaca aagcgcgatt cgatgctatc gagcaggtta tgatttctaa   44040
attcagacag gctttcgggt ccagtgagta cagctacgcg catgtcggtc acttgcacca   44100
ccagaagatt gtagaatccc gtaacatgat tgttgaacag cacaggacgc ttgccgcgaa   44160
agacgcatat gcaagccgcg gcggttggat gtccggtcgt agtgccaacg tcatcacata   44220
cagcgccaat tacggcgaag tggcgcgctt aaccattagc ccggaaatgt tgaagtaacg   44280
gcaaccagta atccgcccag cctgccgatt tggtgggctt ttttgtgcct gt           44332
```